US011561280B2

(12) United States Patent
Belskikh et al.

(10) Patent No.: US 11,561,280 B2
(45) Date of Patent: Jan. 24, 2023

(54) USER IDENTIFICATION DEVICE AND METHOD USING RADIO FREQUENCY RADAR

(71) Applicant: Samsung Electronics Co., Ltd., Suwon-si (KR)

(72) Inventors: Aleksandr Vladimirovich Belskikh, Serpukhov (RU); Mikhail Vyacheslavovich Popov, Krasnogorsk (RU); Stanislav Vladimirovich Polonsky, Moscow (RU); Maksim Alekseyevich Vilensky, Moscow (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 364 days.

(21) Appl. No.: 16/627,019

(22) PCT Filed: Aug. 10, 2018

(86) PCT No.: PCT/KR2018/009155
§ 371 (c)(1),
(2) Date: Dec. 27, 2019

(87) PCT Pub. No.: WO2019/039780
PCT Pub. Date: Feb. 28, 2019

(65) Prior Publication Data
US 2020/0225320 A1 Jul. 16, 2020

(30) Foreign Application Priority Data

Aug. 24, 2017 (RU) .......................... RU2017129907
Aug. 3, 2018 (KR) ........................ 10-2018-0090902

(51) Int. Cl.
*G06K 5/00* (2006.01)
*G01S 7/41* (2006.01)
(Continued)

(52) U.S. Cl.
CPC .......... *G01S 7/412* (2013.01); *G01S 13/0209* (2013.01); *G06K 7/10366* (2013.01);
(Continued)

(58) Field of Classification Search
CPC ........ G06N 20/00; G06N 3/04; G06N 3/0445; G01S 13/0209; G06K 7/10366;
(Continued)

(56) References Cited

U.S. PATENT DOCUMENTS 5,892,838 A 4/1999 Brady
7,123,752 B2 10/2006 Kato et al.
(Continued)

FOREIGN PATENT DOCUMENTS

EP 1408443 B1 10/2006
EP 2698686 A2 2/2014
(Continued)

OTHER PUBLICATIONS

International Search Report dated Dec. 31, 2018, issued in International Patent Application No. PCT/KR2018/009155.
(Continued)

*Primary Examiner* — Daniel St Cyr
(74) *Attorney, Agent, or Firm* — Jefferson IP Law, LLP

(57) ABSTRACT

A user identification device according to a disclosed embodiment includes a transmitter for scattering radio-frequency (RF) signals into tissues of a body part of a user, a receiver for receiving the RF signals having passed through the tissues of the body part of the user, a memory for storing parameters of a trained classification algorithm, and a processor for identifying the user by analyzing the received RF signals based on the trained classification algorithm by using the parameters of the trained classification algorithm in response to receiving the RF signals through the receiver.

15 Claims, 13 Drawing Sheets

(51) Int. Cl.
*G06N 20/00* (2019.01)
*G01S 13/02* (2006.01)
*G06K 7/10* (2006.01)
*G06K 19/07* (2006.01)
*G16H 40/67* (2018.01)

(52) U.S. Cl.
CPC ......... *G06K 19/0723* (2013.01); *G06N 20/00* (2019.01); *G16H 40/67* (2018.01)

(58) Field of Classification Search
CPC ...... G06K 30/06; G06Q 10/087; G06Q 20/40; G06Q 20/42
USPC ........................ 235/380, 382, 462.46, 472.02
See application file for complete search history.

(56) References Cited

U.S. PATENT DOCUMENTS

| | | | |
|---|---|---|---|
| 7,333,090 | B2 | 2/2008 | Tanaka et al. |
| 9,251,691 | B2 | 2/2016 | Wilmeth et al. |
| 9,329,767 | B1 | 5/2016 | Teller et al. |
| 9,427,190 | B1 | 8/2016 | Proud |
| 9,542,579 | B2 | 1/2017 | Mangold et al. |
| 10,013,822 | B2 | 7/2018 | Kim et al. |
| 2004/0068409 | A1 | 4/2004 | Tanaka et al. |
| 2006/0215883 | A1 | 9/2006 | Kim et al. |
| 2008/0001735 | A1* | 1/2008 | Tran ............... A61B 5/6803 340/539.22 |
| 2008/0139899 | A1 | 6/2008 | Student et al. |
| 2008/0183388 | A1 | 7/2008 | Goodrich |
| 2010/0321229 | A1 | 12/2010 | Dwelly et al. |
| 2011/0054360 | A1 | 3/2011 | Son et al. |
| 2012/0066168 | A1 | 3/2012 | Fadell et al. |
| 2014/0028546 | A1 | 1/2014 | Jeon et al. |
| 2014/0055352 | A1 | 2/2014 | Davis et al. |
| 2014/0095852 | A1 | 4/2014 | Levi et al. |
| 2014/0335490 | A1 | 11/2014 | Baarman et al. |
| 2014/0378787 | A1 | 12/2014 | Brumback et al. |
| 2015/0009116 | A1 | 1/2015 | Mangold et al. |
| 2015/0068069 | A1* | 3/2015 | Tran ............... A43B 3/34 340/693.1 |
| 2015/0073235 | A1 | 3/2015 | Kateraas et al. |
| 2015/0230761 | A1 | 8/2015 | Brumback et al. |
| 2015/0301606 | A1 | 10/2015 | Andrei |
| 2015/0349810 | A1 | 12/2015 | Baxley et al. |
| 2015/0350233 | A1 | 12/2015 | Baxley et al. |
| 2015/0350902 | A1 | 12/2015 | Baxley et al. |
| 2016/0042169 | A1 | 2/2016 | Polehn |
| 2016/0054792 | A1 | 2/2016 | Poupyrev |
| 2016/0054803 | A1 | 2/2016 | Poupyrev |
| 2016/0062320 | A1 | 3/2016 | Chung |
| 2016/0089052 | A1 | 3/2016 | Cho et al. |
| 2016/0091980 | A1 | 3/2016 | Baranski et al. |
| 2016/0195928 | A1 | 7/2016 | Wagner et al. |
| 2016/0228052 | A1 | 8/2016 | Proud |
| 2016/0247380 | A1 | 8/2016 | Kumar |
| 2016/0306932 | A1 | 10/2016 | Fateh et al. |
| 2016/0310004 | A1 | 10/2016 | Proud |
| 2016/0313801 | A1 | 10/2016 | Wagner et al. |
| 2016/0347325 | A1 | 12/2016 | Phillips |
| 2017/0031449 | A1 | 2/2017 | Karsten et al. |
| 2017/0086256 | A1 | 3/2017 | Chen et al. |
| 2017/0090567 | A1 | 3/2017 | Allec et al. |
| 2017/0158202 | A1 | 6/2017 | Yang |

FOREIGN PATENT DOCUMENTS

| | | |
|---|---|---|
| EP | 3118762 A1 | 1/2017 |
| JP | 2003-248664 A | 9/2003 |
| KR | 20110043993 A | 4/2011 |
| KR | 10-2017-0009086 A | 1/2017 |
| RU | 2292079 C2 | 1/2007 |
| WO | 2016/053459 A1 | 4/2016 |
| WO | 2016/170005 A1 | 10/2016 |
| WO | 2017/052957 A1 | 3/2017 |

OTHER PUBLICATIONS

Russian Search Report dated Apr. 4, 2018, issued in Russian Patent Application No. 2017129907.
Russian Decision on Grant dated Dec. 17, 2018, issued in Russian Patent Application No. 2017129907.
Russian Notification on Results of Estimation of Patentability of Invention dated Apr. 6, 2018, Russian Patent Application No. 2017129907.
Russian Office Action dated Aug. 10, 2018, Issued in Russian Patent Application No. 2017129907.
Extended European Search Report dated Apr. 24, 2020, issued in European Patent Application No. 18847466.2-1115.
European Search Report dated Oct. 20, 2022, issued in European Application No. 18847466.2.

* cited by examiner

USER IDENTIFICATION DEVICE AND METHOD USING RADIO FREQUENCY RADAR

TECHNICAL FIELD

The disclosure relates to user identification, and more particularly, to a user identification device and method using radio-frequency (RF) radar.

BACKGROUND ART

A technology for obtaining biometric data of a user by using radio-frequency (RF) radar is known in the art.

For example, US 2016054792 A1 published on Feb. 25, 2016 and entitled "Radar-Based Biometric Recognition" discloses a technology for measuring biometric characteristics, but user identification may not be achieved using biometric characteristics measured according to this patent application.

US 2016089052 A1 published on Mar. 31, 2016 and entitled "Method and device for measuring biometric data using UWB radar" discloses a technology for collecting biometric data by using ultra-wideband (UWB) radar, but user identification may not be achieved using biometric data collected according to this patent application.

DESCRIPTION OF EMBODIMENTS

Technical Problem

A user identification technology capable of easily identifying a user and preventing user identification information from being easily counterfeited is required.

Solution to Problem

Provided are a device and method of obtaining biometric data of a user by using radio-frequency (RF) radar, and identifying the user based on the obtained biometric data of the user.

Advantageous Effects of Disclosure

Continuous user identification may be achieved to provide information for identifying a user at any time, and spoof-proof continuous authentication may be performed without an additional security process.

BRIEF DESCRIPTION OF DRAWINGS

The above and other aspects, features, and advantages of certain embodiments of the disclosure will be more apparent from the following description taken in conjunction with the accompanying drawings.

BEST MODE

Figure 1:
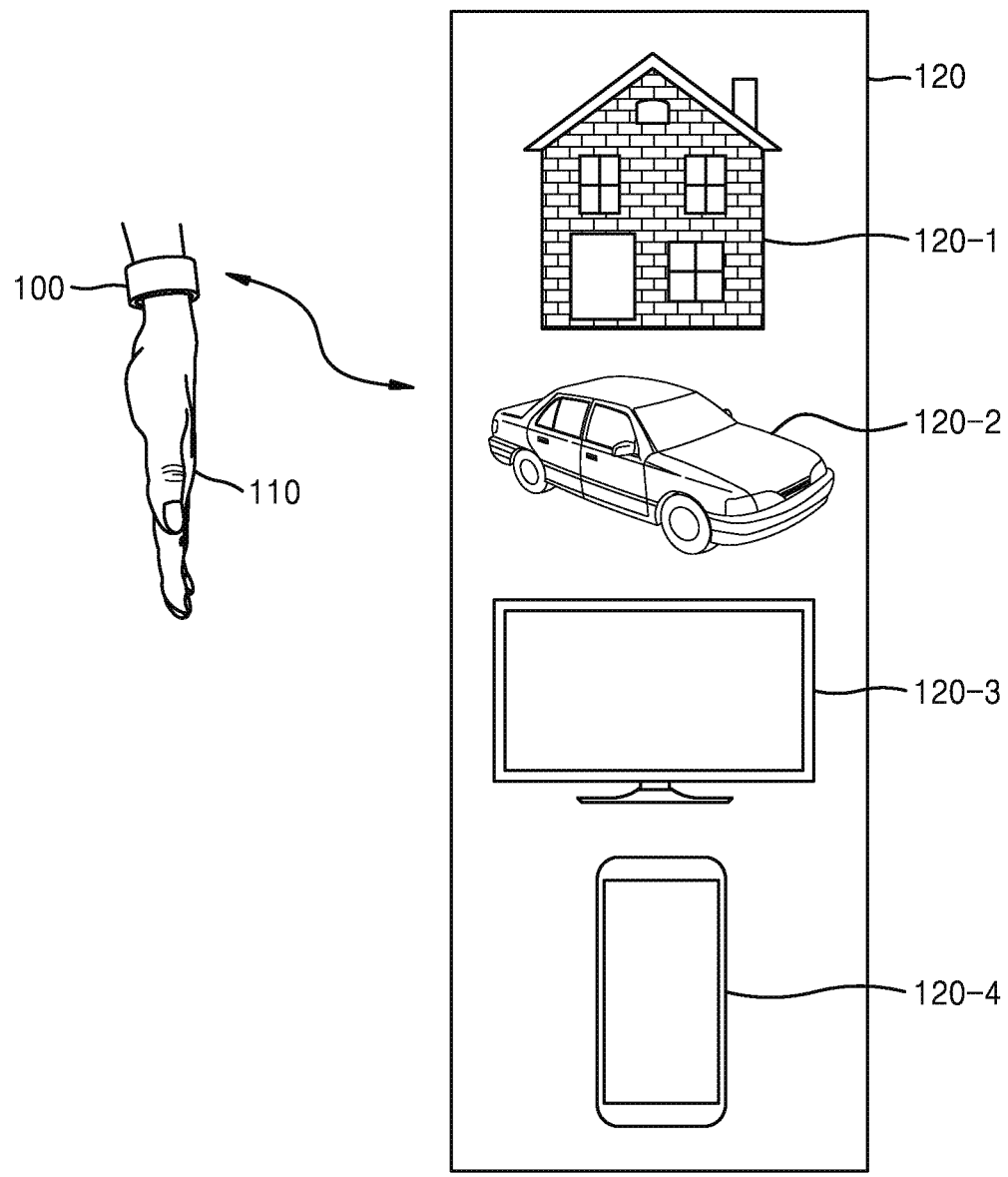
FIG. 1 is a schematic diagram of a user identification device according to an embodiment.

According to an embodiment of the disclosure, a user identification device using radio-frequency (RF) radar includes a transmitter for transmitting RF signals into a body part of a user, a receiver for receiving the RF signals transmitted from the transmitter and having passed through the body part of the user, a memory for storing parameters of a classification algorithm trained with the RF signals having passed through the body part of the user, and a processor for identifying the user by analyzing the received RF signals based on the trained classification algorithm by using the parameters in response to receiving the RF signals having passed through the body part, through the receiver.

According to an embodiment of the disclosure, a user identification method performed by a device by using radio-frequency (RF) radar includes generating, by a transmitter of the device, RF signals and scattering the generated RF signals into a body part of a user, receiving, by a receiver of the device, the RF signals having passed through the body part of the user, and identifying the user by analyzing the received RF signals based on a trained classification algorithm executed by a processor of the device, by using parameters of the classification algorithm trained in response to receiving the RF signals having passed through the body part of the user.

According to an embodiment of the disclosure, a computer-readable recording medium has recorded thereon a program for executing the user identification method.

MODE OF DISCLOSURE

Various embodiments of the disclosure will now be described in detail with reference to the attached drawings. However, the disclosure may be embodied in many different forms and should not be construed as being limited to the structures and functions set forth herein. The embodiments of the disclosure are provided so that this disclosure will be thorough and complete. It will be understood by one of ordinary skill in the art that technical features of the disclosure support each or a combination of embodiments of the disclosure. For example, a method or a device according to the disclosure may be provided by a combination of an arbitrary number of embodiments of the disclosure. Embodiments of the disclosure may be implemented by one or more elements described in the claims. That is, parts of an embodiment and another embodiment of the disclosure may be combined to operate the device.

Terms and languages used in the following description and the claims are not limited to bibliographic meanings but may be simply used by the inventors to provide clear and consistent understanding of the disclosure. Therefore, it should be understood by one of ordinary skill in the art that the following description of various embodiments of the disclosure is provided for illustrative purposes only.

As used herein, the term 'an embodiment' (or exemplary) is used "illustratively or for explanation". In the following description, "an embodiment" is not construed as being necessarily preferred compared to other embodiments. As used herein, the singular forms are intended to include the plural forms as well, unless the context clearly indicates otherwise.

The terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

FIG. 1 is a schematic diagram of a user identification device 100 according to an embodiment. The user identification device 100 illustrated in FIG. 1 is configured as a device wearable on a wrist of a user 110, but the user identification device 100 of the disclosure is not limited thereto. For example, the user identification device 100 of the disclosure may be configured as a device wearable on a body part of the user 110, e.g., the head, neck, nose, ear, waist, ankle, or body of the user 110.

As such, the user identification device 100 may be represented as a wearable device having a user identification function. The wearable device may include, for example, devices based on clothes such as gloves, suits, shirts, trousers (or pants), and hats, or devices based on accessories such as glasses, earrings, bracelets, ankle bracelets, watches, necklaces, necklace headsets, and helmets, but is not limited thereto.

When the user 110 wears the user identification device 100, the user identification device 100 scatters radio-frequency (RF) signals into tissues of the wrist of the user 110. The tissues of the wrist of the user 110 may indicate a body part of the user 110. The scattered RF signals may be ultra-wideband signals ranging, for example, from 1 GHz to 15 GHz, but is not limited thereto. The scattering of the RF signals may indicate scattering of ultra-wideband signals. The scattering of the RF signals may indicate emitting of the RF signals.

The user identification device 100 receives the RF signals having passed through the tissues of the wrist of the user 110. To memorize the user 110, the user identification device 100 may obtain parameters by training a classification algorithm with the RF signals received for a certain time. The classification algorithm may be based on a neural network of any architecture, logistic regression, a decision tree, a support vector machine, a method of K nearest neighbors, a naïve Bayesian classifier, or an arbitrary combination of the above-mentioned classification algorithms, but is not limited thereto. The classification algorithm may be referred to as a classifier or a classification means. The parameters obtained by training the classification algorithm include reference values, variables, or information used to classify the received RF signals into RF signals for the user 110. Therefore, the parameters obtained by training the classification algorithm are used to analyze the received RF signals to identify the user 110. The user identification device 100 may collect the RF signals having passed through the tissues of the wrist of the user 110 for the certain time, and obtain the parameters by training the classification algorithm with the collected RF signals.

The user identification device 100 may obtain the parameters by training the classification algorithm with the RF signals received based on a plurality of gestures of the user 110. The user identification device 100 stores the parameters obtained by training the classification algorithm, in the user identification device 100 and reads and uses the parameters stored in the user identification device 100, to analyze the RF signals having passed through the body part of the user 110, based on the trained classification algorithm.

Figure 2:
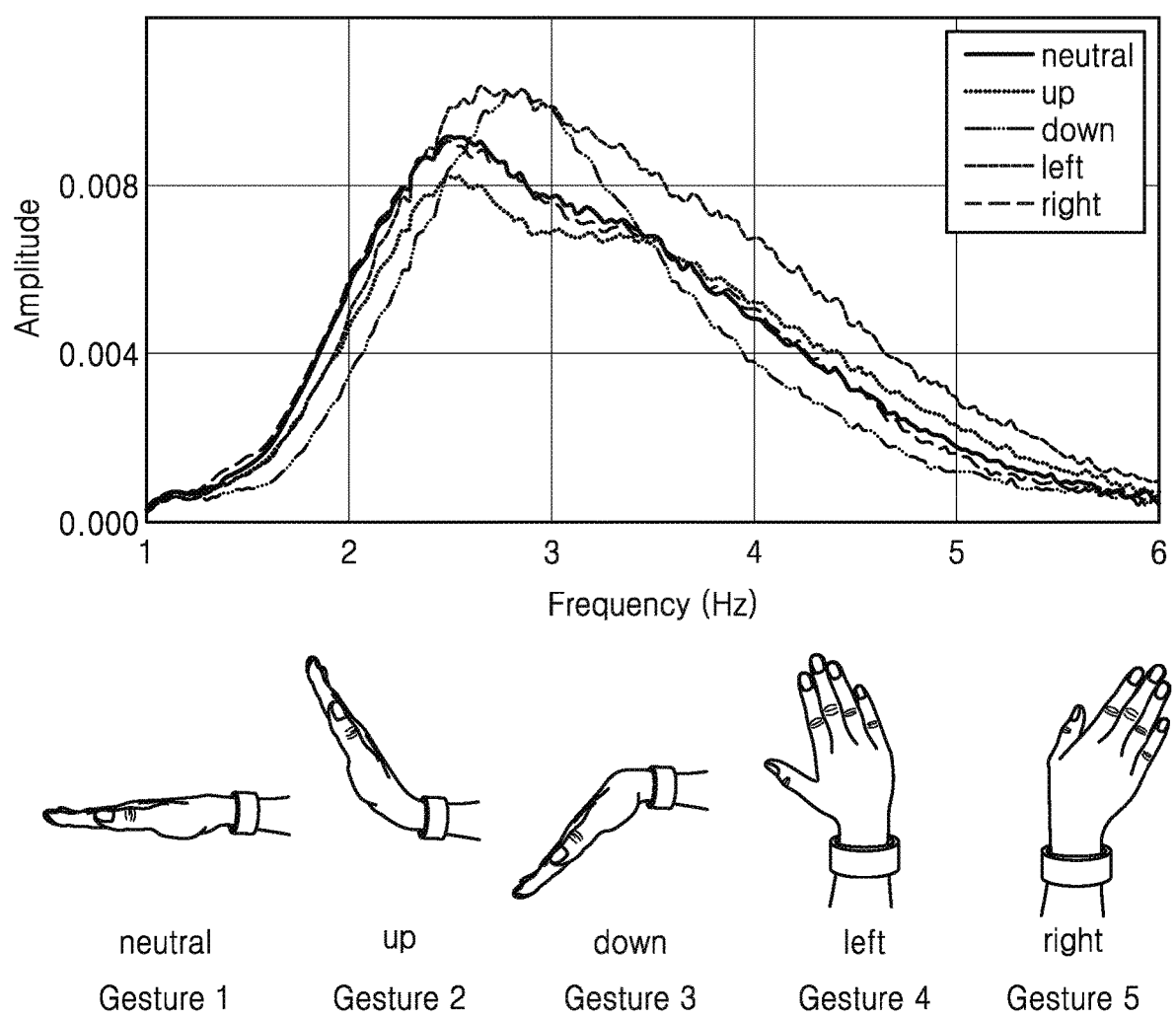
FIG. 2 illustrates an example of radio-frequency (RF) signals having passed through tissues of a wrist of a user, based on a plurality of gestures of the user.

FIG. 2 illustrates an example of RF signals having passed through tissues of a wrist of the user 110 based on a plurality of gestures of the user 110. The RF signals illustrated in FIG. 2 may be referred to as RF signals having passed through a specific body part of the user 110 based on a plurality of gestures of the specific body part.

Referring to FIG. 2, the plurality of gestures of the user 110 may include, for example, gesture 1 indicating that a hand of the user 110 is in a neutral position, gesture 2 indicating that the hand of the user 110 is in an up position, gesture 3 indicating that the hand of the user 110 is in a down position, gesture 4 indicating that the hand of the user 110 is in a left position, and gesture 5 indicating that the hand of the user 110 is in a right position, but the plurality of gestures of the user 110 is not limited thereto.

Referring to FIG. 2, the RF signals having passed through the wrist of the user 110 are distorted differently depending on the gestures of the user 110. The distortion of the RF signals is shown as, for example, attenuation (amplitude variations) of the RF signals and phase shift of the RF signals. The user identification device 100 may identify the user 110 or identify the user 110 and a user gesture based on the RF signals having passed through the wrist of the user 110 and corresponding to the gestures of the user 110.

As the user gesture is identified, the user identification device 100 may perform an operation corresponding to the user gesture, or transmit a command corresponding to the user gesture, to an external device 120. The user identification device 100 may, for example, set different user commands, different authentication ranges, or/and different control ranges for different user gestures.

For example, when the user gesture indicates that the hand of the user 110 is in a neutral position, the user identification device 100 may set information about the user gesture in such a manner that a smart home 120-1 is unlocked based on a signal transmitted from the user identification device 100 to the smart home 120-1. When the user gesture indicates that the hand of the user 110 is in an up position, the user identification device 100 may set information about the user gesture in such a manner that a smart car 120-2 is unlocked based on a signal transmitted from the user identification device 100 to the smart car 120-2.

When the user gesture indicates that the hand of the user 110 is in a right position, the user identification device 100 may set information about the user gesture in such a manner that a smart Internet of things (IoT) device 120-3 is turned on based on a signal transmitted from the user identification device 100 to the smart IoT device 120-3. When the user gesture indicates that the hand of the user 110 is in a left position, the user identification device 100 may set information about the user gesture in such a manner that the smart IoT device 120-3 is turned off based on a signal transmitted from the user identification device 100 to the smart IoT device 120-3.

When the user gesture indicates that the hand of the user 110 is in a down position, the user identification device 100 may set information about the user gesture in such a manner that a user authentication process for payment is performed by a smartphone 120-4 based on a signal transmitted from the user identification device 100 to the smartphone 120-4.

The configuration of different user commands, different authentication ranges, or/and different control ranges for different user gestures in the disclosure is not limited to the above-described example.

Figure 3:
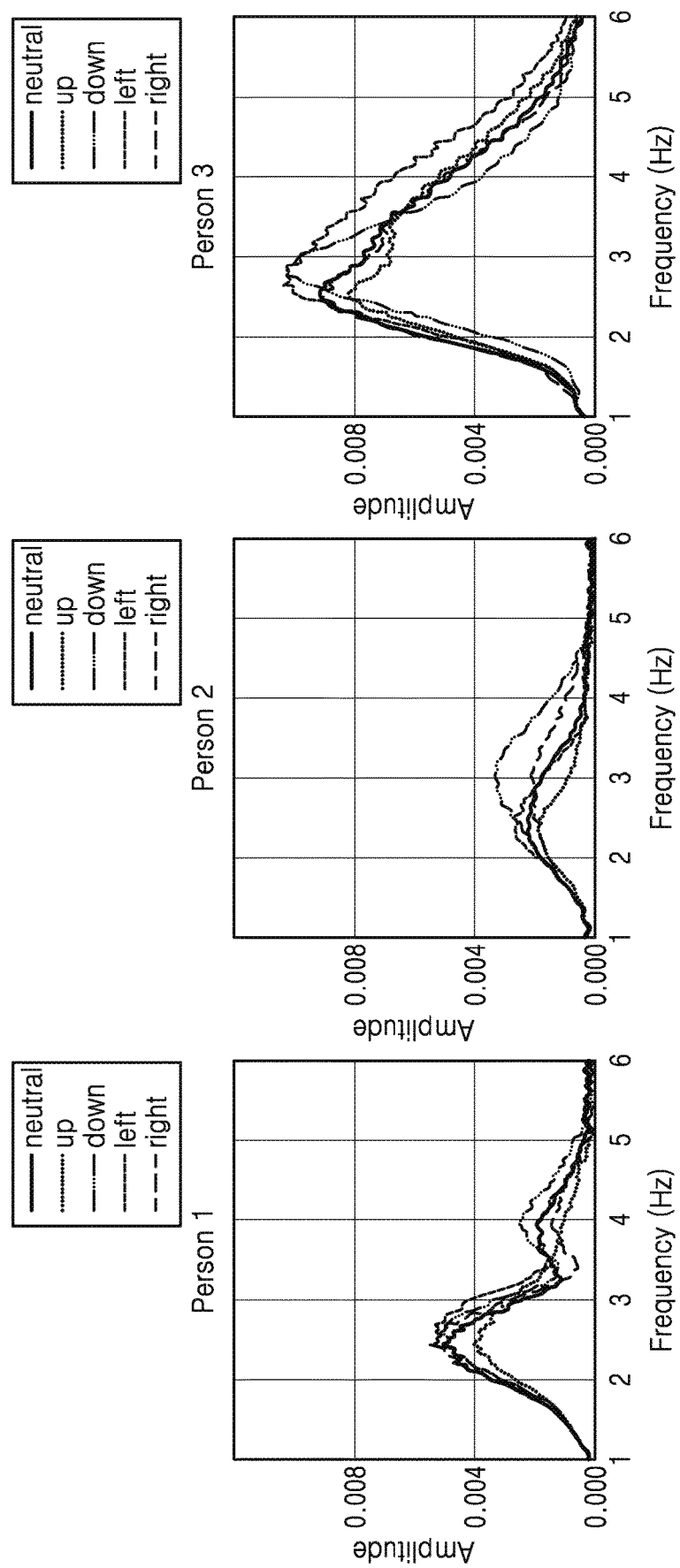
FIG. 3 illustrates an example of RF signals having passed through tissues of wrists of different persons, based on a plurality of gestures of the different persons.

FIG. 3 illustrates an example of RF signals having passed through tissues of wrists of different persons based on a plurality of gestures of the different persons. FIG. 3 illustrates an example of RF signals having passed through tissues of wrists of three persons based on five user gestures (or wrist gestures) illustrated in FIG. 2. Referring to FIG. 3, it is shown that the RF signals having passed through tissues of the same body part are distorted differently depending on the persons and the gestures.

The example of the RF signals illustrated in FIG. 3 shows that the RF signals having passed through tissues of the same body part of the different persons are distorted differently and that, when the tissues of the body part moves due to user gestures, the RF signals having passed through the tissues of the body part are distorted differently depending on the user gestures. This is because different persons have different tissues such as muscles or tendons even at the same body part. Locations of muscles, tendons, or the like of the body part may be changed due to the gestures, and the RF signals having passed through the tissues of the body part may be distorted due to the change in muscles, tendons, or the like. For example, the locations of muscles, tendons, or the like of a wrist of person 1 may differ in gesture 1, gesture 2, gesture 3, gesture 4, and gesture 5 of person 1.

Therefore, the RF signals having passed through the tissues of the body part of each person may be recognized as unique biometric data of the person, and thus the user identification device 100 may identify a user based on the RF signals having passed through the tissues of the body part of each person. In the disclosure, user identification may be referred to as biometric user identification or biometric user authentication. In the disclosure, biometric user authentication may indicate checking of a right of the user 110 to access the external device 120, based on the biometric data (i.e., the RF signals) obtained by the user identification device 100.

In the disclosure, a user gesture may be used as an authentication key of a user. A plurality of user gestures may be predetermined. Therefore, the plurality of user gestures may be referred to as predetermined gestures or predetermined calibration gestures.

After the parameters of the trained classification algorithm are stored, when the user 110 re-wears or continuously wears the user identification device 100, the user identification device 100 scatters RF signals into the tissues of the wrist of the user 110 and receives the RF signals having passed through the tissues of the wrist of the user 110. The user identification device 100 analyzes the received RF signals by using the parameters of the trained classification algorithm, and identifies the user 110 or/and a user gesture.

The user identification result obtained by the user identification device 100 may indicate whether the user 110 is an owner of the user identification device 100. The user identification device 100 may transmit the user identification result to the external device 120. The user identification result transmitted to the external device 120 may indicate a positive user identification result. The positive user identification result may indicate that the user 110 is the owner of the user identification device 100. The user identification result transmitted from the user identification device 100 to the external device 120 may include identified user information (e.g., authentication information).

The user identification result indicating that the user 110 is not the owner of the user identification device 100 may indicate a negative user identification result. When the user identification result is negative, the user identification device 100 may not transmit the user identification result to the external device 120. When the user identification result indicates that the user 110 is not the owner of the user identification device 100, the user identification device 100 may forbid the user 110 wearing the user identification device 100, from accessing the external device 120.

When the user identification result indicates that the user 110 is the owner of the user identification device 100, the user identification device 100 may request the external device 120 to allow the user 110 to access the external device 120. Assuming that the external device 120 is the smart home 120-1, being allowed to access the external device 120 may indicate that a door is unlocked when the user 110 wearing the user identification device 100 arrives at the smart home 120-1.

Assuming that the external device 120 is the smart car 120-2, being allowed to access the external device 120 may indicate that the smart car 120-2 is unlocked when the user 110 wearing the user identification device 100 approaches the smart car 120-2. Assuming that the external device 120 is the smart car 120-2, being allowed to access the external device 120 may indicate that the smart car 120-2 sets driving conditions personalized for the user 110 when the user 110 wearing the user identification device 100 gets in the smart car 120-2.

Being allowed to access the external device 120 may indicate that a temperature, lightings, a music volume, etc. of a home are automatically set based on an environment personalized for the user 110 when the user 110 wearing the user identification device 100 is at home. Being allowed to access the external device 120 may indicate that a smart device such as a smartphone, a tablet, or a TV is unlocked without fingerprint or iris scan. Being allowed to access the external device 120 may indicate that personal tickets for various events may be issued or a payment system may be easily accessed without an additional authentication procedure.

As described above, the user 110 may perform a user authentication procedure in all applications requiring user authentication, by merely wearing the user identification device 100 without performing an additional operation for authenticating the user 110, e.g., iris scan, fingerprint scan, pin code input, or password input. As such, the user 110 may be connected to an event requiring various authentications, by merely wearing the user identification device 100 without performing an additional authentication procedure, and does not need to show an identification (ID) to authenticate the user 110.

The user identification device 100 may store parameters of a classification algorithm trained for a plurality of users, and equally or differently set access levels to the external device 120 for the plurality of users. For example, when parameters of a classification algorithm trained to identify user 1, user 2, and user 3 are stored, the user identification device 100 may set the access levels to the external device 120 in such a manner that user 1, user 2, and user 3 may unlock the smart home 120-1 and user 1 may unlock the smart car 120-2. In addition, the user identification device 100 may set the access levels to the external device 120 in such a manner that user 1, user 2, and user 3 may access different payment systems.

As described above, using the user identification device 100 according to the disclosure, all applications requiring user authentication may be used without performing an additional authentication procedure. User authentication in all applications may be performed based on a result of user identification performed according to the disclosure. The user identification device 100 may continuously identify and authenticate the user 110 while the user 110 is wearing the user identification device 100.

The user identification device 100 according to the disclosure may be used to use a smart home, to use a payment system, to access various devices such as a mobile phone, a smartphone, and a computer, to access various electronic services, and to unlock various smart devices.

Using the user identification device 100 according to the disclosure, the user 110 does not need to perform a login or unlock operation whenever access to a device, a network, or a payment system is attempted. In addition, using the user identification device 100 according to the disclosure, the user 110 may perform spoof-proof continuous authentication without an additional security process. This is because the user identification device 100 according to the disclosure identifies the user 110 by using biometric data of the user 110. Using the user identification device 100 according to the disclosure, the user 110 may register user identification information only once to perform seamless access without performing re-login in an IoT network environment.

The external device 120 illustrated in FIG. 1 may be an arbitrary device for providing electronic devices accessible for user authentication, or an arbitrary device accessible through user authentication. The external device 120 may include an external user authentication device. The external device 120 may include the smart home 120-1, the smart car 120-2, the IoT device 120-3, and the smartphone 120-4 as illustrated in FIG. 1, but is not limited thereto. For example, the external device 120 may further include a payment system or a device capable of notifying occurrence of an event. The event may include an event related to a purchase, e.g., a purchase of a product or a purchase of a ticket, but is not limited thereto.

Figure 4:
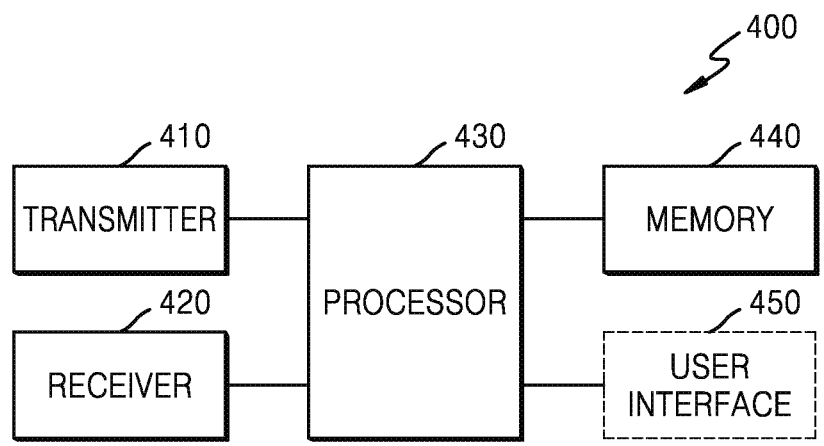
FIG. 4 is a block diagram of a user identification device according to an embodiment.

FIG. 4 is a block diagram of a user identification device 400 according to an embodiment.

Referring to FIG. 4, the user identification device 400 may include a transmitter 410, a receiver 420, a processor 430, and a memory 440, but the elements of the user identification device 400 are not limited thereto. For example, the user identification device 400 may further include a user interface 450.

The transmitter 410 may generate RF signals and scatter the generated RF signals into a body part of a user. The transmitter 410 may be controlled by the processor 430 to generate the RF signals and scatter the generated RF signals into the body part of the user. Regardless of the control of the processor 430, when the user wears the user identification device 400, the transmitter 410 may generate the RF signals and scatter the generated RF signals into the body part of the user.

A sensor (not shown) of the user identification device 400 may detect whether the user is wearing the user identification device 400, and the detection result may be transmitted to the transmitter 410 to enable operation of the transmitter 410. The detection result of the sensor may be transmitted to the processor 430, and the processor 430 may control operation of the transmitter 410 based on the detection result. Determining of whether the user is wearing the user identification device 400 may be performed based on a user input indicating that the user identification device 400 is worn, but is not limited thereto. The user input indicating that the user identification device 400 is worn may include a user input for turning on the user identification device 400.

The transmitter 410 may scatter ultra-wideband RF signals ranging from 1 GHz to 15 GHz, but the frequency band of the scattered RF signals is not limited thereto. The transmitter 410 may include a transmit antenna for scattering the RF signals.

The receiver 420 receives the RF signals having passed through the body part of the user. The receiver 420 may receive the ultra-wideband RF signals having passed through the body part of the user. The receiver 420 may include a receive antenna or a receive sensor for receiving the RF signals having passed through the body part of the user. The receiver 420 may be controlled by the processor 430 to receive the RF signals. Operation of the receiver 420 may be enabled based on a signal detected by a sensor (not shown) for detecting whether the user identification device 400 is worn. The processor 430 may control operation of the receiver 420 based on the signal detected by the sensor.

The processor 430 trains a classification algorithm with the RF signals received though the receiver 420, and obtains parameters of the trained classification algorithm. The processor 430 stores the obtained parameters in the memory 440. After the parameters are stored in the memory 440, when RF signals are received through the receiver 420, the processor 430 identifies the user by analyzing the received RF signals based on the trained classification algorithm by reading the parameters stored in the memory 440.

When the parameters of the classification algorithm are obtained, the processor 430 may request the user to make at least one predetermined user gesture, through the user interface 450. Like a touchscreen, the user interface 450 may be configured to have a function of receiving a user input and outputting information. The user interface 450 may be configured to be controlled by the processor 430 to request the user to make at least one predetermined user gesture, by using an audio signal or/and an image signal.

The processor 430 may output the user identification result through the user interface 450. The user identification result output through the user interface 450 may have a form of an alarm, a text message, or/and an image, but is not limited thereto. The alarm may be represented by an audio signal or/and light. The user identification result output through the user interface 450 may indicate that identification is completed or is being performed. The user identification result output through the user interface 450 may indicate whether the user wearing the user identification device 400 is an owner of the user identification device 400.

When the user identification device 400 is integrated with a wearable device of the user, the user interface 450 may be a user interface of the wearable device. When the user identification device 400 is integrated with a wearable device of the user, the processor 430 may be a processor of the wearable device. The processor 430 may be referred to as a central processing unit (CPU) for controlling overall functions of the user identification device 400.

The memory 440 may store the parameters obtained by training the classification algorithm with the received RF signals. The memory 440 may store a program or/and an application including one or more instructions executed by the user identification device 400 according to the disclosure to train the classification algorithm with the received RF signals, obtain the parameters of the trained classification algorithm, identify the user by using the obtained parameters, and use or transmit the user identification result when wearing of the user identification device 400 by the user is recognized. The memory 440 may store the RF signals received through the receiver 420 for a certain time. The processor 430 may obtain the parameters by training the classification algorithm by reading the RF signals stored in the memory 440.

The memory 440 may include at least one type of a storage medium from among flash memory, a hard disk, a multimedia card micro, a memory card (e.g., a secure digital (SD) or extreme digital (XD) card), random access memory (RAM), static RAM (SRAM), read-only memory (ROM), electrically erasable programmable ROM (EEPROM), programmable ROM (PROM), magnetic memory, a magnetic disc, and an optical disc.

The processor 430 may perform a user identification method according to the disclosure by executing the program or/and the application stored in the memory 440. The processor 430 may include a converter for converting the RF signals received from the receiver 420, into digital signals. When the processor 430 does not include the above-described converter, the receiver 420 may include a converter for converting the received RF signals into digital signals.

The user identification device 400 illustrated in FIG. 4 may be configured to further include various sensors such as an accelerometer sensor, a gyroscope sensor, and a magnetometer sensor. When the user identification device 400 further includes the above-mentioned various sensors, the user identification device 400 may use detection results of the above-mentioned various sensors to more accurately identify the user gesture and/or the user.

Figure 5:
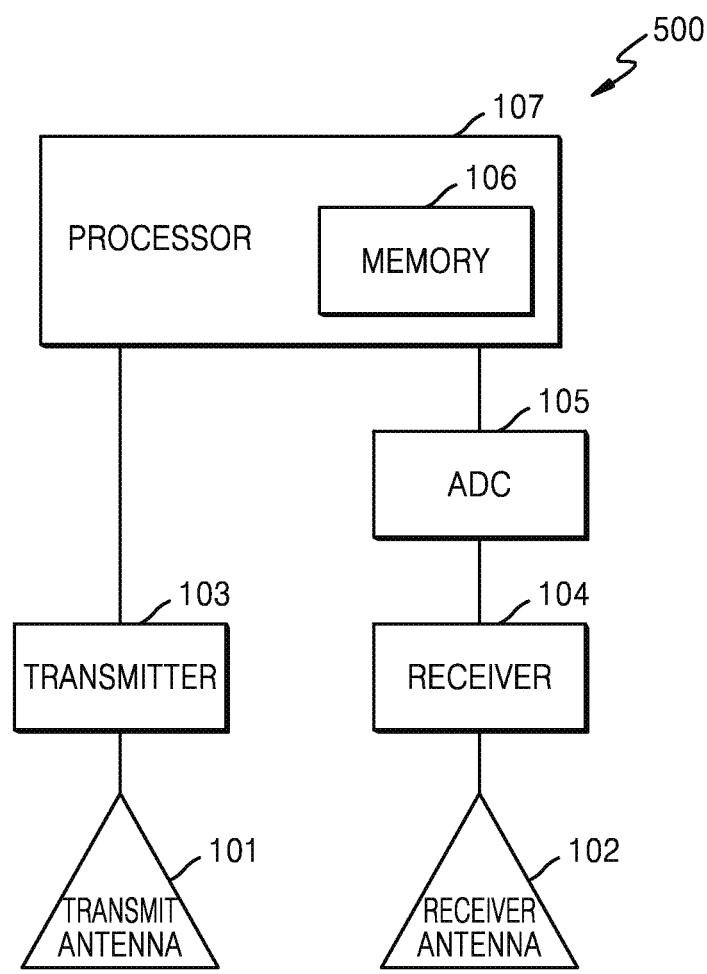
FIG. 5 is a block diagram of a user identification device according to another embodiment.

FIG. 5 is a block diagram of a user identification device 500 according to another embodiment. Referring to FIG. 5, the user identification device 500 includes a transmit antenna 101, a receive antenna 102, a transmitter 103, a receiver 104, an analog/digital converter (ADC) 105, a memory 106, and a processor 107. In the disclosure, an RF radar may include the transmit antenna 101, the receive antenna 102, the transmitter 103, the receiver 104, and the ADC 105. The processor 107 may be configured and operate like the processor 430 illustrated in FIG. 4. The memory 106 may be configured and operate like the memory 440 illustrated in FIG. 4.

The user identification device 500 includes one transmit antenna 101, one receive antenna 102, one transmitter 103, one receiver 104, and one ADC 105 in FIG. 5, the user identification device 500 may include a plurality of transmit antennas 101, a plurality of receive antennas 102, a plurality of transmitters 103, a plurality of receivers 104, and a plurality of ADCs 105. The receive antenna 102 illustrated in FIG. 5 may be configured as a receive sensor. The transmit antenna 101 and the receive antenna 102 may be placed adjacent to the transmitter 103 and the receiver 104, respectively.

In FIG. 5, the processor 107 includes the memory 106. The memory 106 may be separate from the processor 107. The memory 106 may include an arbitrary-type computer-recordable storage device and/or an arbitrary computer-recordable storage medium. The memory 106 stores parameters of a trained classification algorithm. The memory 106 may be configured like the memory 440 illustrated in FIG. 4. When the processor 107 is an external processor of the user identification device 500, digital signals output from the ADC 105 may be transmitted to the external processor. The external processor may be a processor of a device integrated with the user identification device 500, but is not limited thereto.

The transmit antenna 101 may be connected to the transmitter 103, and the receive antenna 102 may be connected to the receiver 104. The transmit antenna 101 may scatter ultra-wideband signals. The receive antenna 102 may receive ultra-wideband signals. The transmit antenna 101 and the receive antenna 102 may be placed at an inner side of the user identification device 500 and at opposite sides of a body part of a user when the user wears the user identification device 500, but are not limited thereto.

Figure 6:
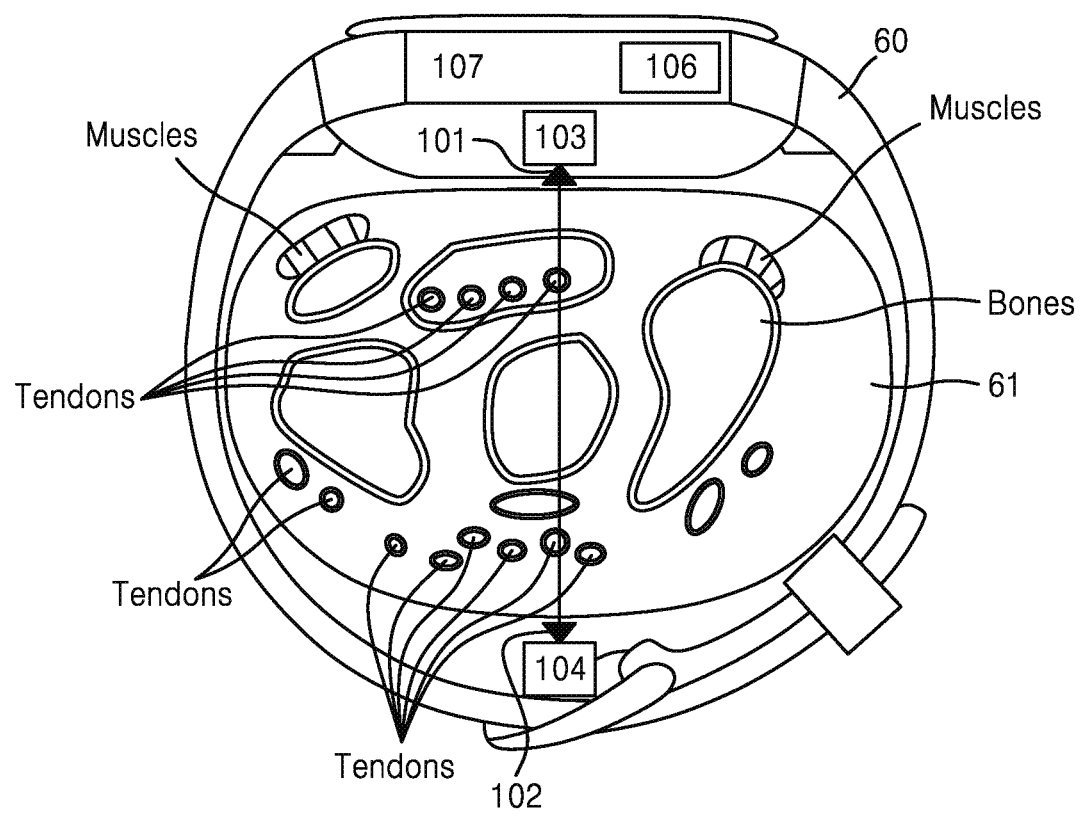
FIG. 6 illustrates an example of placement of elements included in the user identification device illustrated in FIG. 5.

FIG. 6 illustrates an example of placement of elements included in the user identification device 500 illustrated in FIG. 5. Referring to FIG. 6, the user identification device 500 is integrated with a watch 60. Therefore, in FIG. 6, the watch 60 integrated with the user identification device 500 may be worn on a wrist 61 of a user. In FIG. 6, the transmit antenna 101 and the receive antenna 102 are placed at an inner side of the watch 60 and at opposite sides when the user wears the watch 60.

In the disclosure, a device integrable with the user identification device 500 is not limited to the watch 60. The device integrable with the user identification device 500 may include the devices mentioned above in relation to FIG. 1. Locations and the numbers of the transmit antennas 101 and the receive antennas 102 may be determined depending on the device integrated with the user identification device 500.

Figure 7:
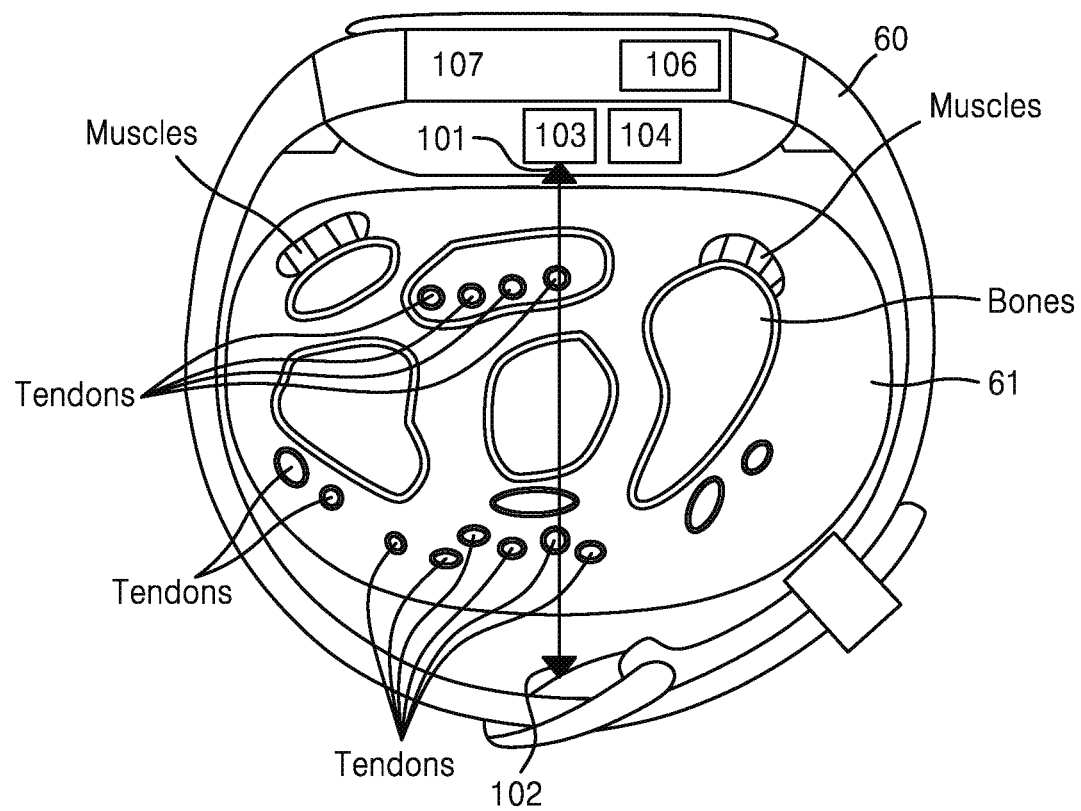
FIG. 7 illustrates another example of placement of elements included in the user identification device illustrated in FIG. 5.

FIG. 7 illustrates another example of placement of elements included in the user identification device 500 illustrated in FIG. 5. Referring to FIG. 7, the transmit antenna 101 and the receive antenna 102 may be placed as illustrated in FIG. 6 but the transmitter 103 and the receiver 104 may be placed adjacent to each other. The transmitter 103 and the receiver 104 may be configured as an integrated transceiver.

When a user wears the user identification device 500, the transmitter 103 generates ultra-wideband signals and scatters the ultra-wideband signals through the transmit antenna 101 into tissues of a body part of the user. The transmitter 103 may be configured to operate in a range from 1 GHz to 15 GHz.

The scattered ultra-wideband signals pass through tissues of the body part of the user. At the same time, the tissues of the body part of the user distort the ultra-wideband signals. The distortion of the received ultra-wideband signals is shown as, for example, attenuation (amplitude variations) of the RF signals and phase shift of the RF signals. The receiver 104 receives the signals distorted as described above through the body part of the user.

The ADC 105 is connected to the receiver 104. The ADC 105 converts the signals received by the receiver 104, into digital signals to be provided to the processor 107. The processor 107 identifies the user by analyzing the received digital signals by using the parameters of the trained classification algorithm stored in the memory 106.

The processor 107 obtains parameters for identifying the user, by training the classification algorithm stored in the memory 106, with the received RF signals, and stores the obtained parameters in the memory 106. After the parameters are stored in the memory 106, the processor 107 obtains a user identification result by analyzing the received RF signals based on the trained classification algorithm by reading the parameters stored in the memory 106. A technology known in the art is used to analyze the RF signals based on the trained classification algorithm by using the parameters of the trained classification algorithm.

Optionally, the processor 107 may pre-process the received RF signals before analyzing the RF signals. The pre-processing may include various mathematical transformations of received data, e.g., averaging, moving average, moving median, signal value scaling in total frequency range, wavelet transform, Fourier transform, taking the logarithm, exponent, exponentiation, multiplication/division by a constant, subtraction/addition of a constant, a differential, and an integral, signal conversion from a complex number into an amplitude phase indication and an inverse conversion thereof, and noise filtering of one or more received digital signals to remove obvious outliers from a dataset obtained together with errors as a result of interference, or a resultant dataset such as calculation errors. The pre-processing is well known in the art and thus a detailed description thereof will now be provided herein. The user identification device 500 may be configured to perform the above-described pre-processing between the ADC 105 and the processor 107. The above-described pre-processing may also be performed on the RF signals received to train the classification algorithm.

Figure 8:
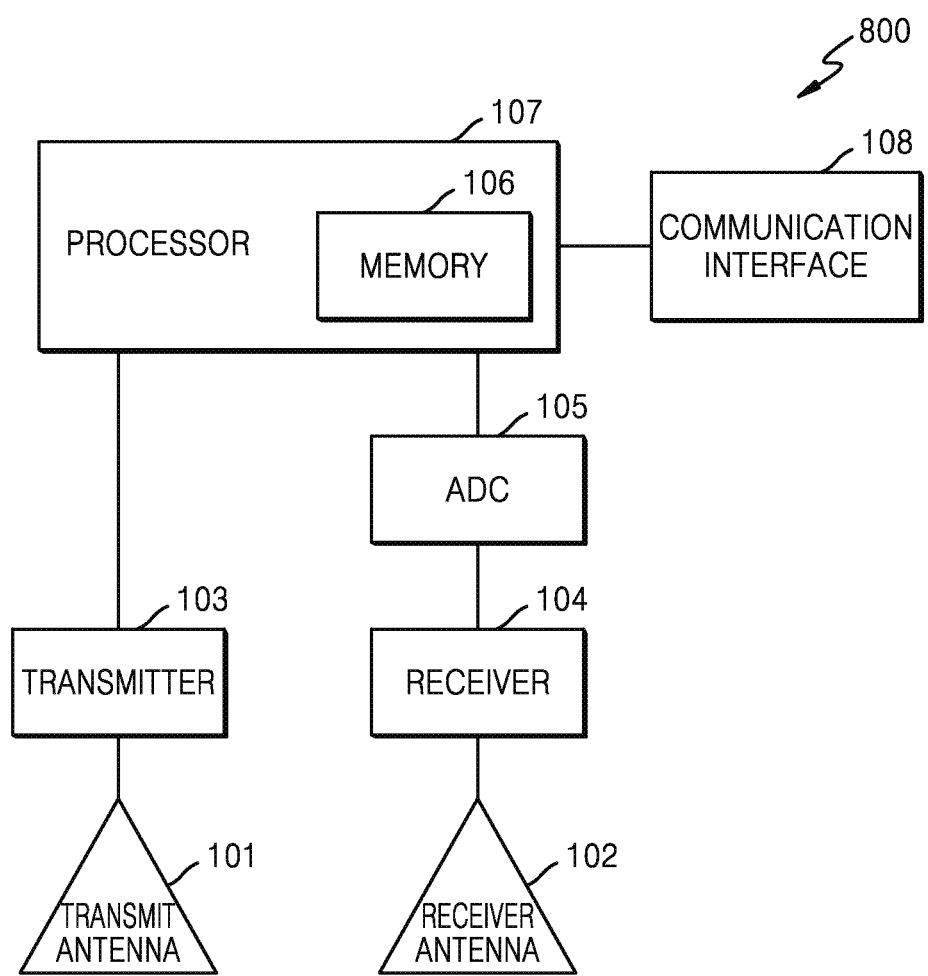
FIG. 8 is a block diagram of a user identification device according to another embodiment.

FIG. 8 is a block diagram of a user identification device 800 according to another embodiment.

Referring to FIG. 8, the user identification device 800 further includes a communication interface 108 compared to the user identification device 500 of FIG. 5. The communication interface 108 may be referred to as an auxiliary transmitter. The communication interface 108 may transmit a user identification result to the external device 120 illustrated in FIG. 1. The communication interface 108 may transmit digital signals output from the ADC 105, to the external device 120. When the processor 107 is an external processor of the user identification device 800, the digital signals output from the ADC 105 may be transmitted to the external processor.

The communication interface 108 may transmit or receive data to or from the external device 120 based on short-range wireless communication. The short-range wireless communication may include, for example, Bluetooth communication, Bluetooth low energy (BLE) communication, near field communication (NFC), wireless local area network (WLAN) (or Wi-Fi) communication, Zigbee communication, infrared data association (IrDA) communication, Wi-Fi direct (WFD) communication, ultra-wideband (UWB) communication, and adaptive network topology+(ANT+) communication, but is not limited thereto. For example, the communication interface 108 may be configured based on wired communication. The communication interface 108 may transmit data received from the external device 120, to the processor 107. The processor 107 may transmit user information stored in the memory 106, through the communication interface 108 to the external device 120 based on the data received from the communication interface 108. The processor 107 may transmit a user identification result through the communication interface 108 to the external device 120 based on the data received from the communication interface 108. The user identification result transmitted through the communication interface 108 to the external device 120 may include the user identification result outputtable through the user interface 450 of FIG. 4.

Figure 9:
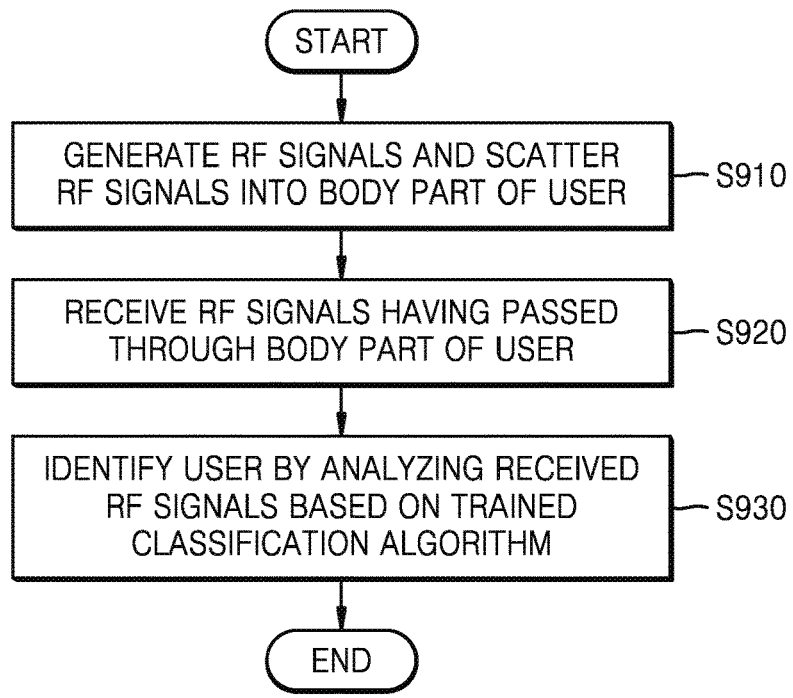
FIG. 9 is a flowchart of a user identification method according to an embodiment.

FIG. 9 is a flowchart of a user identification method according to an embodiment. The user identification method illustrated in FIG. 9 will be described based on the user identification device 100 illustrated in FIG. 1, but may also be performed by the user identification devices 400, 500, and 800 illustrated in FIGS. 4 to 8.

In operation S910, the user identification device 100 generates RF signals and scatters the generated RF signals into a body part of the user 110. For example, in the user identification device 100, the transmitter 103 generates the RF signals and scatters the generated RF signals through the transmit antenna 101 into the body part of the user 110. The RF signals scattered into the body part of the user 110 are ultra-wideband signals ranging from 1 GHz to 15 GHz, but the frequency band of the scattered RF signals is not limited thereto. When the user 110 wears the user identification device 100, the user identification device 100 may perform operation S910. Determining of whether the user 110 wears the user identification device 100 may be performed as described above in relation to FIG. 1. Operation S910 is performed after the user identification device 100 stores parameters obtained by training a classification algorithm with the RF signals having passed through the body part of the user 110.

In operation S920, the user identification device 100 receives the RF signals having passed through the body part of the user 110. For example, the user identification device 100 receives the RF signals having passed through the body part of the user 110, through the receive antenna 102 or a receive sensor. When the RF signals scattered from the user identification device 100 are ultra-wideband signals ranging from 1 GHz to 15 GHz, the received RF signals are ultra-wideband signals ranging from 1 GHz to 15 GHz.

In operation S930, the user identification device 100 identifies the user 110 by analyzing the received RF signals based on the trained classification algorithm by using the stored parameters of the trained classification algorithm. The analyzing of the received RF signals based on the trained classification algorithm may indicate classifying of the received RF signals by using the parameters, and determining of whether the classified RF signals correspond to the RF signals having passed through the body part of the user 110. When the classified RF signals correspond to the RF signals having passed through the body part of the user 110, the user identification device 100 obtains a user identification result indicating that the user 110 wearing the user identification device 100 is an owner of the user identification device 100.

Figure 10:
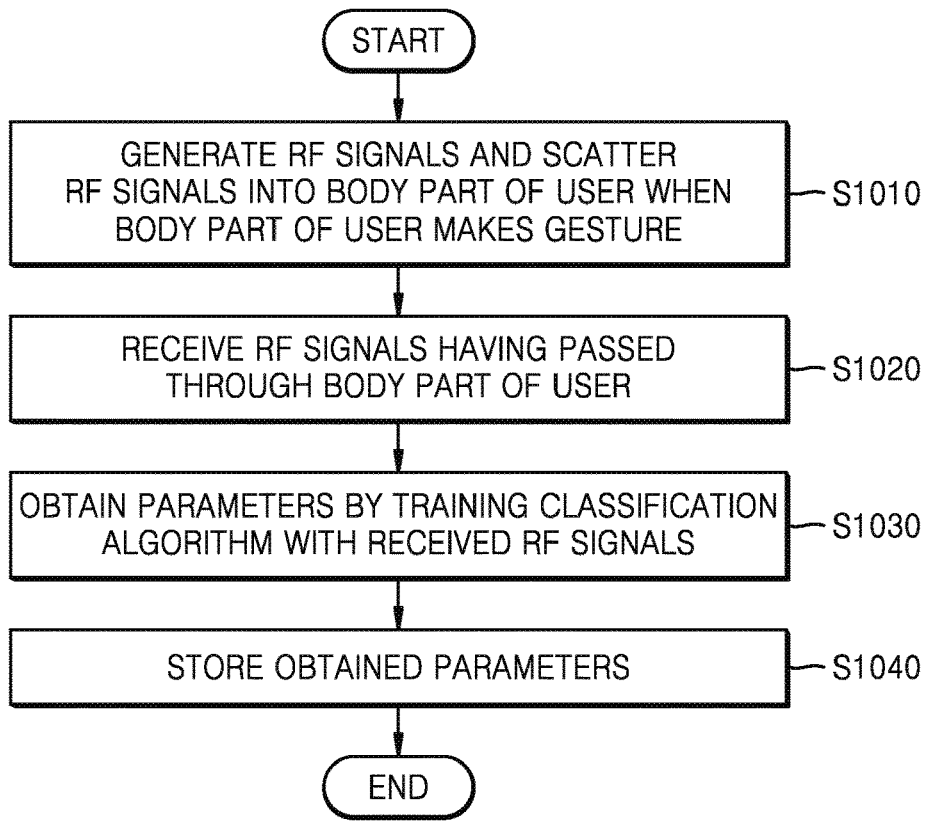
FIG. 10 is a flowchart of a classification algorithm training process in a user identification method, according to an embodiment.

FIG. 10 is a flowchart of a classification algorithm training process in a user identification method, according to an embodiment. The process of FIG. 10 may be performed before the user identification method illustrated in FIG. 9 is performed, but is not limited thereto. The process of FIG. 10 may be performed when a user wears the user identification device 100 for the first time. The process of FIG. 10 may be performed on each of a plurality of users. When the process of FIG. 10 is performed on a plurality of users, the user identification device 100 may identify the plurality of users. The process of FIG. 10 may be performed on each of a plurality of gestures of one user. The user may register at least one of the plurality of gestures as a unique signature of the user.

In operation S1010, the user identification device 100 generates RF signals and scatters the generated RF signals into a body part of the user 110 when the body part of the user 110 makes a gesture. In operation S1010, the user identification device 100 may detect whether the user 110 wears the user identification device 100 and then detect whether the user 110 makes a gesture. To this end, the user identification device 100 may use a sensor included in the user identification device 100. The user identification device 100 may request the user 110 to make a predetermined user gesture, before operation S1010. A method of requesting the user 110 to make a user gesture may be performed using the user interface 450 as described above in relation to FIG. 4.

In operation S1020, the user identification device 100 receives the RF signals having passed through the body part of the user 110. When the RF signals scattered in operation S1010 are ultra-wideband signals ranging from 1 GHz to 15 GHz, the received RF signals are ultra-wideband signals ranging from 1 GHz to 15 GHz and distorted through the body part of the user 110.

In operation S1030, the user identification device 100 trains a classification algorithm with the received RF signals and obtains parameters of the trained classification algorithm. The obtained parameters include reference values, variables, or information used to classify the received RF signals into RF signals corresponding to the user 110 or/and the user gesture, based on the trained classification algorithm.

In operation S1040, the user identification device 100 stores the obtained parameters. When the parameters are stored, the user identification device 100 may further store additional information in such a manner that each or at least one of the plurality of gestures is registered as a unique signature of the user 110. The stored additional information may indicate that the user gesture identified based on the stored parameters is registered as a unique signature of the user 110.

Figure 11:
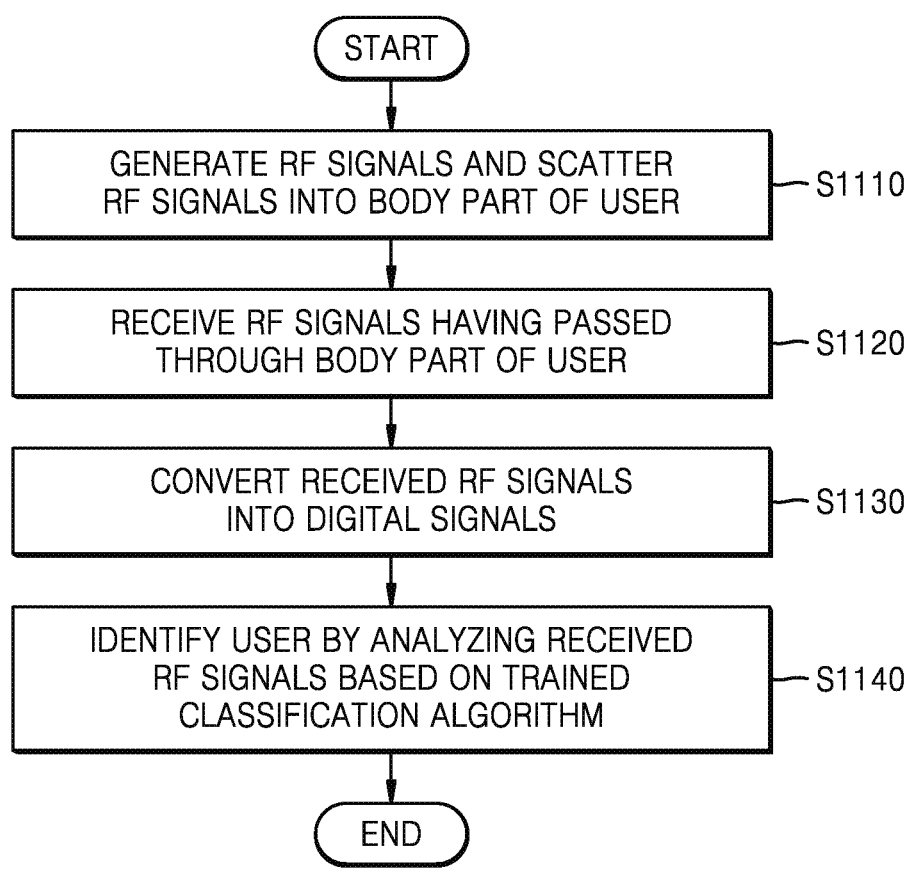
FIG. 11 is a flowchart of a user identification method according to another embodiment.

FIG. 11 is a flowchart of a user identification method according to another embodiment. Operations S1110, S1120, and S1140 illustrated in FIG. 11 are performed similarly to operations S910 to S930 illustrated in FIG. 9.

In operation S1130, the user identification device 100 converts received RF signals into digital signals. In operation S1140, the user identification device 100 identifies the user 110 by analyzing the digital RF signals based on a trained classification algorithm.

Figure 12:
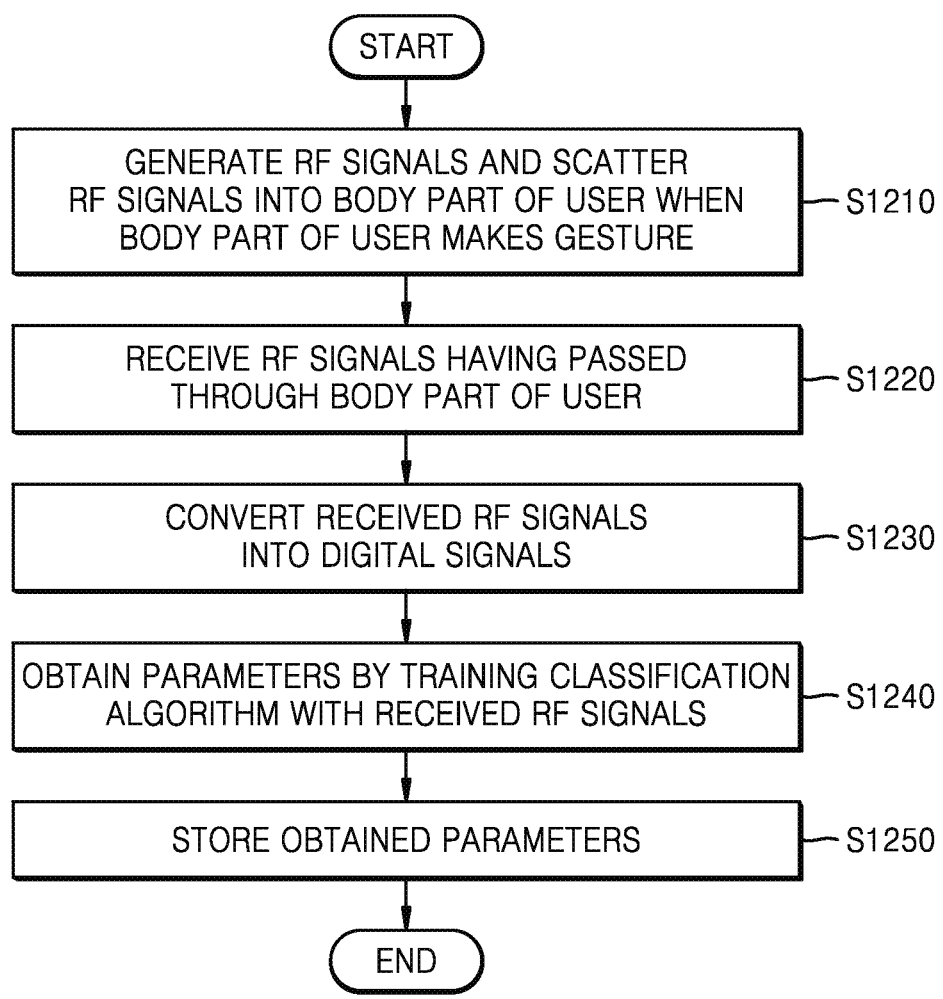
FIG. 12 is a flowchart of a classification algorithm training process in a user identification method, according to another embodiment.

FIG. 12 is a flowchart of a classification algorithm training process in a user identification method, according to another embodiment. Operations S1210, S1220, S1240, and S1250 illustrated in FIG. 12 are performed similarly to operations S1010 to S1040 illustrated in FIG. 10.

In operation S1230, the user identification device 100 converts received RF signals into digital signals. In operation S1240, the user identification device 100 obtains parameters by training a classification algorithm with the digital RF signals.

Figure 13:
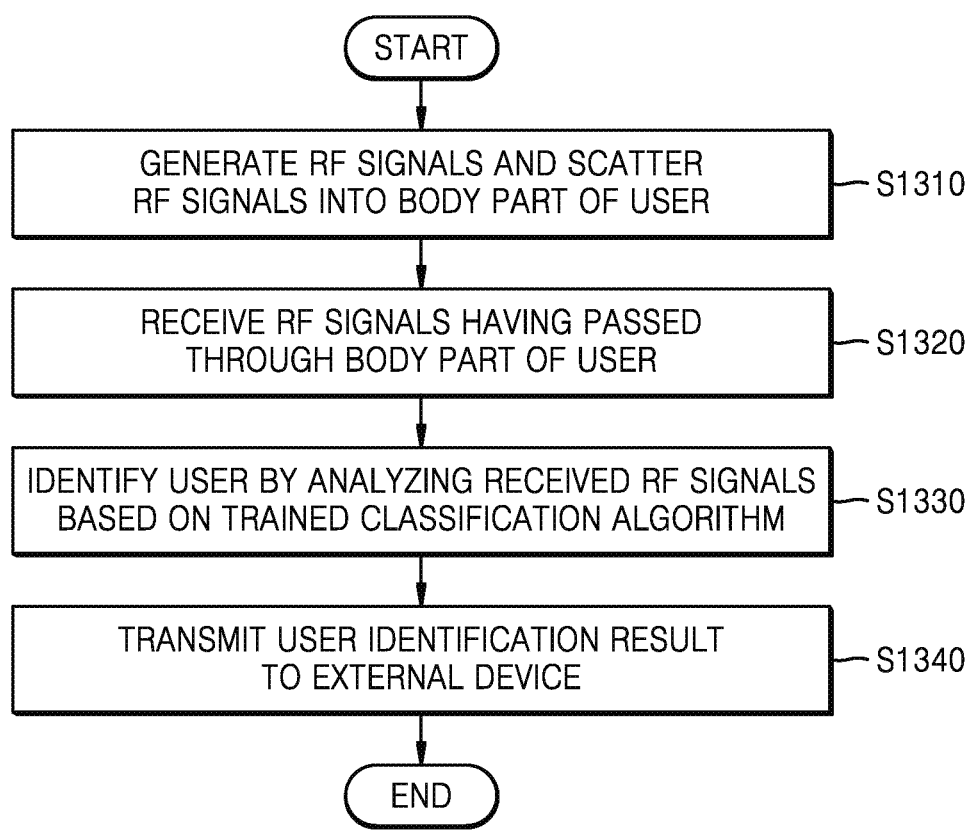
FIG. 13 is a flowchart of a user identification method according to another embodiment.

FIG. 13 is a flowchart of a user identification method according to another embodiment. The method of FIG. 13 further includes an operation of transmitting a user identification result to an external device, compared to the method of FIG. 9. Operations S1310 to S1330 of FIG. 13 are performed similarly to operations S910 to S930 of FIG. 9.

In operation S1340, the user identification device 100 transmits a user identification result to the external device 120. The user identification device 100 may transmit the user identification result to the external device 120 through the communication interface 108 illustrated in FIG. 8. The user identification device 100 may transmit the user identification result to the external device 120 upon a request received through the communication interface 108 from the external device 120. The user identification result may include user authentication information (e.g., user login information or user authentication password information). The user authentication information may be pre-stored in the user identification device 100. The user identification result may replace the user authentication information.

Figure 14:
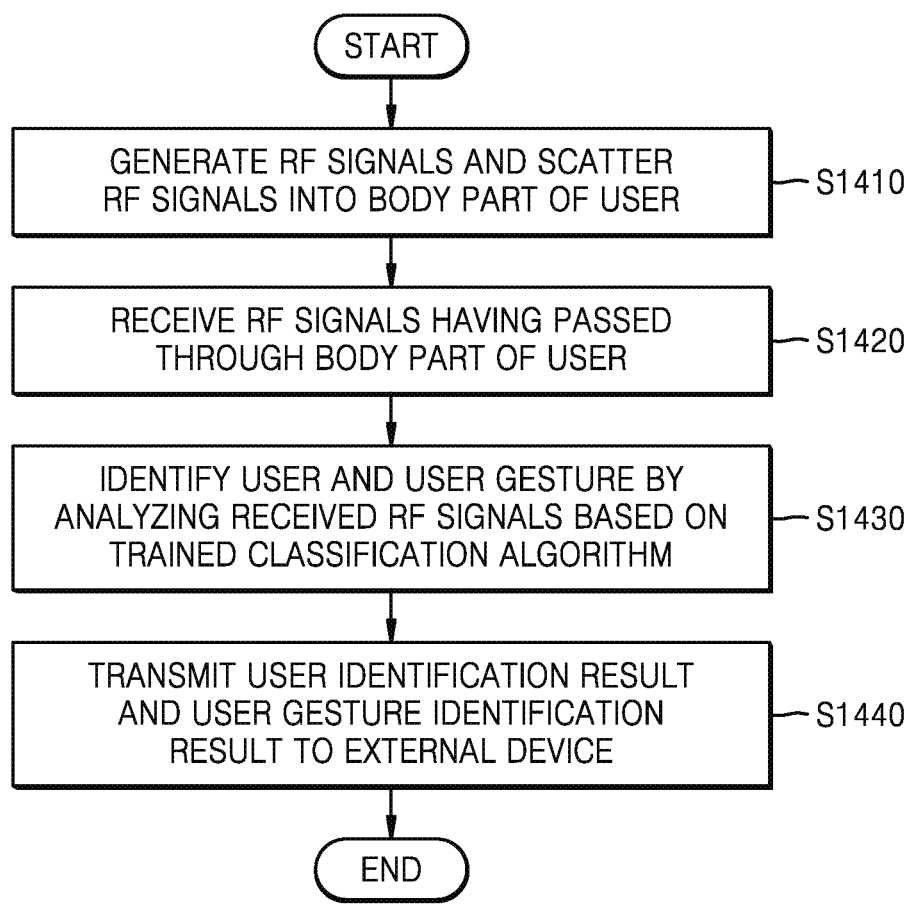
FIG. 14 is a flowchart of a user identification method according to another embodiment.

FIG. 14 is a flowchart of a user identification method according to another embodiment. The method of FIG. 14 further includes an operation of transmitting a user identification result and an identified user gesture to an external device, compared to the method of FIG. 9. Operation S1410 and S1420 of FIG. 14 are performed similarly to operations S910 and S920 of FIG. 9.

In operation S1430, the user identification device 100 identifies the user 110 and a user gesture by analyzing received RF signals based on a trained classification algorithm by using stored parameters. The stored parameters may include information capable of classifying received RF signals per user and per user gesture.

In operation S1440, the user identification device 100 transmits the user identification result and the user gesture identification result through the communication interface 108 of FIG. 8 to the external device 120. When a request is received through the communication interface 108 from the external device 120, the user identification device 100 may transmit the user identification result and the user gesture identification result to the external device 120.

Figure 15:
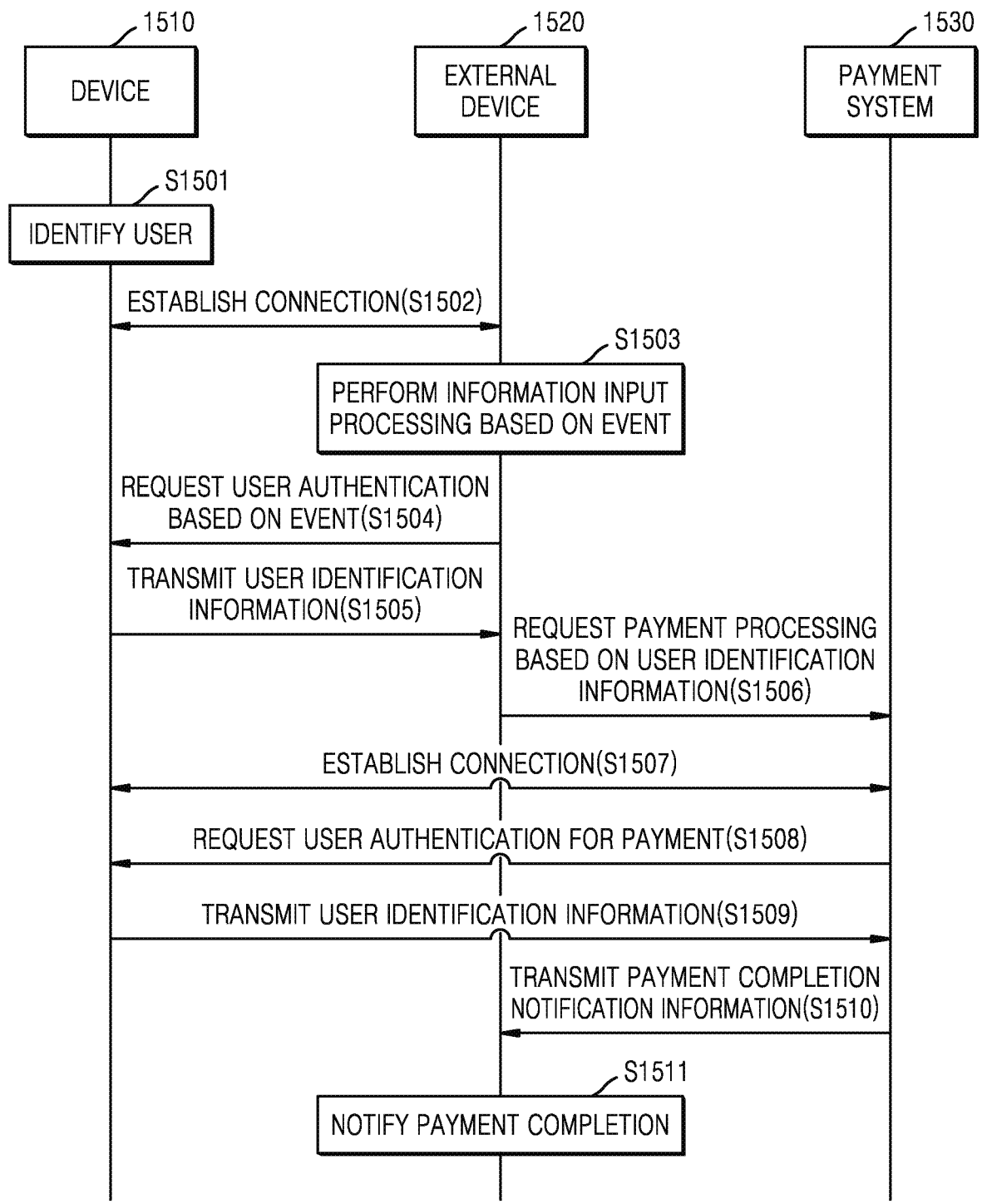
FIG. 15 is a flowchart of a user authentication method based on a user identification result, according to an embodiment.

FIG. 15 is a flowchart of a user authentication method according to an embodiment. The method of FIG. 15 is performed by a device 1510 having a user identification function according to the disclosure, an external device 1520, and a payment system 1530.

In operation S1501, the device 1510 identifies a user by using RF signals according to the disclosure. After the user is identified, a connection between the device 1510 and the external device 1520 is established (S1502), the external device 1520 performs information input processing based on an event (S1503), and the device 1510 receives a user authentication request based on the event (S1504) and transmits user identification information to the external device 1520 (S1505). The user identification information may include user authentication information stored in the device 1510, and may be used as the user authentication information.

The information input processing performed based on the event in operation S1503 may include, for example, information input for ticketing. For example, to get a train ticket, the above-described information may include departure place information, destination information, boarding time information, and passenger information. The above-described information may be directly input to the external device 1520 by the user wearing the device 1510. For example, the external device 1520 may be a smartphone or a ticket machine installed at a train station. The ticket machine may be a device having a communication function. When the external device 1520 is the smartphone, the above-described information input processing may be performed based on a ticketing application executed by the external device 1520. The establishing of the connection between the device 1510 and the external device 1520 in operation S1502 may be performed when the user authentication request is received in operation S1504 after the information input processing is completed in operation S1503. Owners of the external device 1520 and the device 1510 may be the same or be different.

When the user identification information is received from the device 1510, in operation S1506, the external device 1520 transmits a payment processing request based on the user identification information to the payment system 1530. The payment system 1530 may be an Internet-based payment server.

The payment system 1530 obtains information about the device 1510 based on the received user identification information, and establishes a connection between the device 1510 and the payment system 1530 based on the obtained information about the device 1510 (S1507). To this end, the payment system 1530 may include a database storing mapping information between the user identification information and the information about the device 1510. The information about the device 1510 includes information for the connection to the device 1510 based on a communication network such as the Internet.

When the connection to the device 1510 is established, in operation S1508, the payment system 1530 transmits, to the device 1510, a user authentication request for payment. As such, in operation S1509, the device 1510 transmits the user identification information to the payment system 1530. The payment system 1530 performs payment processing base on the user identification information when the user identification information is received from the device 1510, and transmits payment completion notification information to the external device 1520 (S1510) when the payment processing is completed. As such, the external device 1520 outputs a payment completion notification message to notify the user of the device 1510 of completion of payment. The payment system 1530 may transmit the payment completion notification information to the device 1510 together with the external device 1520. The external device 1520 may output the payment completion notification by using an audio signal or/and an image signal.

Technical features of the disclosure will become apparent from the afore-described embodiments and the attached drawings. It will be understood by one of ordinary skill in the art that various changes in form and details may be made in the disclosure without departing from the scope of the disclosure. Therefore, the afore-described embodiments and the attached drawings should be construed as illustrative and not restrictive. Unless otherwise indicated herein, the singular forms in claims are intended to include the plural forms as well.

The afore-described embodiments may be implemented in the form of a computer-readable recording medium having computer-executable instructions and data recorded thereon. The instructions may be stored in the form of program codes, and may generate a predetermined program module to perform a predetermined operation when executed by a processor. In addition, the instructions may perform predetermined operations of the afore-described embodiments when executed by a processor. FIG. 3 illustrates an example of RF signals. FIG. 3 illustrates an example of RF signals having passed through tissues of wrists of three persons based on five user gestures (or wrist gestures) illustrated in FIG. 2. Referring to FIG. 3, it is shown that the RF signals having passed through tissues of the same body part are distorted differently depending on the persons and the gestures.

The example of the RF signals illustrated in FIG. 3 shows that the RF signals having passed through tissues of the same body part of the different persons are distorted differently and that, when the tissues of the body part moves due to user gestures, the RF signals having passed through the tissues of the body part are distorted differently depending on the user gestures. This is because different persons have different tissues such as muscles or tendons even at the same body part. Locations of muscles, tendons, or the like of the body part may be changed due to the gestures, and the RF signals having passed through the tissues of the body part may be distorted due to the change in muscles, tendons, or the like. For example, the locations of muscles, tendons, or the like of a wrist of person 1 may differ in gesture 1, gesture 2, gesture 3, gesture 4, and gesture 5 of person 1.

Therefore, the RF signals having passed through the tissues of the body part of each person may be recognized as unique biometric data of the person, and thus the user identification device 100 may identify a user based on the RF signals having passed through the tissues of the body part of each person. In the disclosure, user identification may be referred to as biometric user identification or biometric user authentication. In the disclosure, biometric user authentication may indicate checking of a right of the user 110 to access the external device 120, based on the biometric data (i.e., the RF signals) obtained by the user identification device 100.

In the disclosure, a user gesture may be used as an authentication key of a user. A plurality of user gestures may be predetermined. Therefore, the plurality of user gestures may be referred to as predetermined gestures or predetermined calibration gestures.

After the parameters of the trained classification algorithm are stored, when the user 110 re-wears or continuously wears the user identification device 100, the user identification device 100 scatters RF signals into the tissues of the wrist of the user 110 and receives the RF signals having passed through the tissues of the wrist of the user 110. The user identification device 100 analyzes the received RF signals by using the parameters of the trained classification algorithm, and identifies the user 110 or/and a user gesture.

The user identification result obtained by the user identification device 100 may indicate whether the user 110 is an owner of the user identification device 100. The user identification device 100 may transmit the user identification result to the external device 120. The user identification result transmitted to the external device 120 may indicate a positive user identification result. The positive user identification result may indicate that the user 110 is the owner of the user identification device 100. The user identification result transmitted from the user identification device 100 to the external device 120 may include identified user information (e.g., authentication information).

The user identification result indicating that the user 110 is not the owner of the user identification device 100 may indicate a negative user identification result. When the user identification result is negative, the user identification device 100 may not transmit the user identification result to the external device 120. When the user identification result indicates that the user 110 is not the owner of the user identification device 100, the user identification device 100 may forbid the user 110 wearing the user identification device 100, from accessing the external device 120.

When the user identification result indicates that the user 110 is the owner of the user identification device 100, the user identification device 100 may request the external device 120 to allow the user 110 to access the external device 120. Assuming that the external device 120 is the smart home 120-1, being allowed to access the external device 120 may indicate that a door is unlocked when the user 110 wearing the user identification device 100 arrives at the smart home 120-1.

Assuming that the external device 120 is the smart car 120-2, being allowed to access the external device 120 may indicate that the smart car 120-2 is unlocked when the user 110 wearing the user identification device 100 approaches the smart car 120-2. Assuming that the external device 120 is the smart car 120-2, being allowed to access the external device 120 may indicate that the smart car 120-2 sets driving conditions personalized for the user 110 when the user 110 wearing the user identification device 100 gets in the smart car 120-2.

Being allowed to access the external device 120 may indicate that a temperature, lightings, a music volume, etc. of a home are automatically set based on an environment personalized for the user 110 when the user 110 wearing the user identification device 100 is at home. Being allowed to access the external device 120 may indicate that a smart device such as a smartphone, a tablet, or a TV is unlocked without fingerprint or iris scan. Being allowed to access the external device 120 may indicate that personal tickets for various events may be issued or a payment system may be easily accessed without an additional authentication procedure.

As described above, the user 110 may perform a user authentication procedure in all applications requiring user authentication, by merely wearing the user identification device 100 without performing an additional operation for authenticating the user 110, e.g., iris scan, fingerprint scan, pin code input, or password input. As such, the user 110 may be connected to an event requiring various authentications, by merely wearing the user identification device 100 without performing an additional authentication procedure, and does not need to show an identification (ID) to authenticate the user 110.

The user identification device 100 may store parameters of a classification algorithm trained for a plurality of users, and equally or differently set access levels to the external device 120 for the plurality of users. For example, when parameters of a classification algorithm trained to identify user 1, user 2, and user 3 are stored, the user identification device 100 may set the access levels to the external device 120 in such a manner that user 1, user 2, and user 3 may unlock the smart home 120-1 and user 1 may unlock the smart car 120-2. In addition, the user identification device 100 may set the access levels to the external device 120 in such a manner that user 1, user 2, and user 3 may access different payment systems.

As described above, using the user identification device 100 according to the disclosure, all applications requiring user authentication may be used without performing an additional authentication procedure. User authentication in all applications may be performed based on a result of user identification performed according to the disclosure. The user identification device 100 may continuously identify and authenticate the user 110 while the user 110 is wearing the user identification device 100.

The user identification device 100 according to the disclosure may be used to use a smart home, to use a payment system, to access various devices such as a mobile phone, a smartphone, and a computer, to access various electronic services, and to unlock various smart devices.

Using the user identification device 100 according to the disclosure, the user 110 does not need to perform a login or unlock operation whenever access to a device, a network, or a payment system is attempted. In addition, using the user identification device 100 according to the disclosure, the user 110 may perform spoof-proof continuous authentication without an additional security process. This is because the user identification device 100 according to the disclosure identifies the user 110 by using biometric data of the user 110. Using the user identification device 100 according to the disclosure, the user 110 may register user identification information only once to perform seamless access without performing re-login in an IoT network environment.

The external device 120 illustrated in FIG. 1 may be an arbitrary device for providing electronic devices accessible for user authentication, or an arbitrary device accessible through user authentication. The external device 120 may include an external user authentication device. The external device 120 may include the smart home 120-1, the smart car 120-2, the IoT device 120-3, and the smartphone 120-4 as illustrated in FIG. 1, but is not limited thereto. For example, the external device 120 may further include a payment system or a device capable of notifying occurrence of an event. The event may include an event related to a purchase, e.g., a purchase of a product or a purchase of a ticket, but is not limited thereto.

FIG. 4 is a block diagram of a user identification device 400 according to an embodiment.

Referring to FIG. 4, the user identification device 400 may include a transmitter 410, a receiver 420, a processor 430, and a memory 440, but the elements of the user identification device 400 are not limited thereto. For example, the user identification device 400 may further include a user interface 450.

The transmitter 410 may generate RF signals and scatter the generated RF signals into a body part of a user. The transmitter 410 may be controlled by the processor 430 to generate the RF signals and scatter the generated RF signals into the body part of the user. Regardless of the control of the processor 430, when the user wears the user identification device 400, the transmitter 410 may generate the RF signals and scatter the generated RF signals into the body part of the user.

A sensor (not shown) of the user identification device 400 may detect whether the user is wearing the user identification device 400, and the detection result may be transmitted to the transmitter 410 to enable operation of the transmitter 410. The detection result of the sensor may be transmitted to the processor 430, and the processor 430 may control operation of the transmitter 410 based on the detection result. Determining of whether the user is wearing the user identification device 400 may be performed based on a user input indicating that the user identification device 400 is worn, but is not limited thereto. The user input indicating that the user identification device 400 is worn may include a user input for turning on the user identification device 400.

The transmitter 410 may scatter ultra-wideband RF signals ranging from 1 GHz to 15 GHz, but the frequency band of the scattered RF signals is not limited thereto. The transmitter 410 may include a transmit antenna for scattering the RF signals.

The receiver 420 receives the RF signals having passed through the body part of the user. The receiver 420 may receive the ultra-wideband RF signals having passed through the body part of the user. The receiver 420 may include a receive antenna or a receive sensor for receiving the RF signals having passed through the body part of the user. The receiver 420 may be controlled by the processor 430 to receive the RF signals. Operation of the receiver 420 may be enabled based on a signal detected by a sensor (not shown) for detecting whether the user identification device 400 is worn. The processor 430 may control operation of the receiver 420 based on the signal detected by the sensor.

The processor 430 trains a classification algorithm with the RF signals received though the receiver 420, and obtains parameters of the trained classification algorithm. The processor 430 stores the obtained parameters in the memory 440. After the parameters are stored in the memory 440, when RF signals are received through the receiver 420, the processor 430 identifies the user by analyzing the received RF signals based on the trained classification algorithm by reading the parameters stored in the memory 440.

When the parameters of the classification algorithm are obtained, the processor 430 may request the user to make at least one predetermined user gesture, through the user interface 450. Like a touchscreen, the user interface 450 may be configured to have a function of receiving a user input and outputting information. The user interface 450 may be configured to be controlled by the processor 430 to request the user to make at least one predetermined user gesture, by using an audio signal or/and an image signal.

The processor 430 may output the user identification result through the user interface 450. The user identification result output through the user interface 450 may have a form of an alarm, a text message, or/and an image, but is not limited thereto. The alarm may be represented by an audio signal or/and light. The user identification result output through the user interface 450 may indicate that identification is completed or is being performed. The user identification result output through the user interface 450 may indicate whether the user wearing the user identification device 400 is an owner of the user identification device 400.

When the user identification device 400 is integrated with a wearable device of the user, the user interface 450 may be a user interface of the wearable device. When the user identification device 400 is integrated with a wearable device of the user, the processor 430 may be a processor of the wearable device. The processor 430 may be referred to as a central processing unit (CPU) for controlling overall functions of the user identification device 400.

The memory 440 may store the parameters obtained by training the classification algorithm with the received RF signals. The memory 440 may store a program or/and an application including one or more instructions executed by the user identification device 400 according to the disclosure to train the classification algorithm with the received RF signals, obtain the parameters of the trained classification algorithm, identify the user by using the obtained parameters, and use or transmit the user identification result when wearing of the user identification device 400 by the user is recognized. The memory 440 may store the RF signals received through the receiver 420 for a certain time. The processor 430 may obtain the parameters by training the classification algorithm by reading the RF signals stored in the memory 440.

The memory 440 may include at least one type of a storage medium from among flash memory, a hard disk, a multimedia card micro, a memory card (e.g., a secure digital (SD) or extreme digital (XD) card), random access memory (RAM), static RAM (SRAM), read-only memory (ROM), electrically erasable programmable ROM (EEPROM), programmable ROM (PROM), magnetic memory, a magnetic disc, and an optical disc.

The processor 430 may perform a user identification method according to the disclosure by executing the program or/and the application stored in the memory 440. The processor 430 may include a converter for converting the RF signals received from the receiver 420, into digital signals. When the processor 430 does not include the above-described converter, the receiver 420 may include a converter for converting the received RF signals into digital signals.

The user identification device 400 illustrated in FIG. 4 may be configured to further include various sensors such as an accelerometer sensor, a gyroscope sensor, and a magnetometer sensor. When the user identification device 400 further includes the above-mentioned various sensors, the user identification device 400 may use detection results of the above-mentioned various sensors to more accurately identify the user gesture and/or the user.

FIG. 5 is a block diagram of a user identification device 500 according to another embodiment. Referring to FIG. 5, the user identification device 500 includes a transmit antenna 101, a receive antenna 102, a transmitter 103, a receiver 104, an analog/digital converter (ADC) 105, a memory 106, and a processor 107. In the disclosure, an RF radar may include the transmit antenna 101, the receive antenna 102, the transmitter 103, the receiver 104, and the ADC 105. The processor 107 may be configured and operate like the processor 430 illustrated in FIG. 4. The memory 106 may be configured and operate like the memory 440 illustrated in FIG. 4.

The user identification device 500 includes one transmit antenna 101, one receive antenna 102, one transmitter 103, one receiver 104, and one ADC 105 in FIG. 5, the user identification device 500 may include a plurality of transmit antennas 101, a plurality of receive antennas 102, a plurality of transmitters 103, a plurality of receivers 104, and a plurality of ADCs 105. The receive antenna 102 illustrated in FIG. 5 may be configured as a receive sensor. The transmit antenna 101 and the receive antenna 102 may be placed adjacent to the transmitter 103 and the receiver 104, respectively.

In FIG. 5, the processor 107 includes the memory 106. The memory 106 may be separate from the processor 107. The memory 106 may include an arbitrary-type computer-recordable storage device and/or an arbitrary computer-recordable storage medium. The memory 106 stores parameters of a trained classification algorithm. The memory 106 may be configured like the memory 440 illustrated in FIG. 4. When the processor 107 is an external processor of the user identification device 500, digital signals output from the ADC 105 may be transmitted to the external processor. The external processor may be a processor of a device integrated with the user identification device 500, but is not limited thereto.

The transmit antenna 101 may be connected to the transmitter 103, and the receive antenna 102 may be connected to the receiver 104. The transmit antenna 101 may scatter ultra-wideband signals. The receive antenna 102 may receive ultra-wideband signals. The transmit antenna 101 and the receive antenna 102 may be placed at an inner side of the user identification device 500 and at opposite sides of a body part of a user when the user wears the user identification device 500, but are not limited thereto.

FIG. 6 illustrates an example of placement of elements included in the user identification device 500 illustrated in FIG. 5. Referring to FIG. 6, the user identification device 500 is integrated with a watch 60. Therefore, in FIG. 6, the watch 60 integrated with the user identification device 500 may be worn on a wrist 61 of a user. In FIG. 6, the transmit antenna 101 and the receive antenna 102 are placed at an inner side of the watch 60 and at opposite sides when the user wears the watch 60.

In the disclosure, a device integrable with the user identification device 500 is not limited to the watch 60. The device integrable with the user identification device 500 may include the devices mentioned above in relation to FIG. 1. Locations and the numbers of the transmit antennas 101 and the receive antennas 102 may be determined depending on the device integrated with the user identification device 500.

FIG. 7 illustrates another example of placement of elements included in the user identification device 500 illustrated in FIG. 5. Referring to FIG. 7, the transmit antenna 101 and the receive antenna 102 may be placed as illustrated in FIG. 6 but the transmitter 103 and the receiver 104 may be placed adjacent to each other. The transmitter 103 and the receiver 104 may be configured as an integrated transceiver.

When a user wears the user identification device 500, the transmitter 103 generates ultra-wideband signals and scatters the ultra-wideband signals through the transmit antenna 101 into tissues of a body part of the user. The transmitter 103 may be configured to operate in a range from 1 GHz to 15 GHz.

The scattered ultra-wideband signals pass through tissues of the body part of the user. At the same time, the tissues of the body part of the user distort the ultra-wideband signals. The distortion of the received ultra-wideband signals is shown as, for example, attenuation (amplitude variations) of the RF signals and phase shift of the RF signals. The receiver 104 receives the signals distorted as described above through the body part of the user.

The ADC 105 is connected to the receiver 104. The ADC 105 converts the signals received by the receiver 104, into digital signals to be provided to the processor 107. The processor 107 identifies the user by analyzing the received digital signals by using the parameters of the trained classification algorithm stored in the memory 106.

The processor 107 obtains parameters for identifying the user, by training the classification algorithm stored in the memory 106, with the received RF signals, and stores the obtained parameters in the memory 106. After the parameters are stored in the memory 106, the processor 107 obtains a user identification result by analyzing the received RF signals based on the trained classification algorithm by reading the parameters stored in the memory 106. A technology known in the art is used to analyze the RF signals based on the trained classification algorithm by using the parameters of the trained classification algorithm.

Optionally, the processor 107 may pre-process the received RF signals before analyzing the RF signals. The pre-processing may include various mathematical transformations of received data, e.g., averaging, moving average, moving median, signal value scaling in total frequency range, wavelet transform, Fourier transform, taking the logarithm, exponent, exponentiation, multiplication/division by a constant, subtraction/addition of a constant, a differential, and an integral, signal conversion from a complex number into an amplitude phase indication and an inverse conversion thereof, and noise filtering of one or more received digital signals to remove obvious outliers from a dataset obtained together with errors as a result of interference, or a resultant dataset such as calculation errors. The pre-processing is well known in the art and thus a detailed description thereof will now be provided herein. The user identification device 500 may be configured to perform the above-described pre-processing between the ADC 105 and the processor 107. The above-described pre-processing may also be performed on the RF signals received to train the classification algorithm.

FIG. 8 is a block diagram of a user identification device 800 according to another embodiment.

Referring to FIG. 8, the user identification device 800 further includes a communication interface 108 compared to the user identification device 500 of FIG. 5. The communication interface 108 may be referred to as an auxiliary transmitter. The communication interface 108 may transmit a user identification result to the external device 120 illustrated in FIG. 1. The communication interface 108 may transmit digital signals output from the ADC 105, to the external device 120. When the processor 107 is an external processor of the user identification device 800, the digital signals output from the ADC 105 may be transmitted to the external processor.

The communication interface 108 may transmit or receive data to or from the external device 120 based on short-range wireless communication. The short-range wireless communication may include, for example, Bluetooth communication, Bluetooth low energy (BLE) communication, near field communication (NFC), wireless local area network (WLAN) (or Wi-Fi) communication, Zigbee communication, infrared data association (IrDA) communication, Wi-Fi direct (WFD) communication, ultra-wideband (UWB) communication, and adaptive network topology+(ANT+) communication, but is not limited thereto. For example, the communication interface 108 may be configured based on wired communication. The communication interface 108 may transmit data received from the external device 120, to the processor 107. The processor 107 may transmit user information stored in the memory 106, through the communication interface 108 to the external device 120 based on the data received from the communication interface 108. The processor 107 may transmit a user identification result through the communication interface 108 to the external device 120 based on the data received from the communication interface 108. The user identification result transmitted through the communication interface 108 to the external device 120 may include the user identification result outputtable through the user interface 450 of FIG. 4.

FIG. 9 is a flowchart of a user identification method according to an embodiment. The user identification method illustrated in FIG. 9 will be described based on the user identification device 100 illustrated in FIG. 1, but may also be performed by the user identification devices 400, 500, and 800 illustrated in FIGS. 4 to 8.

In operation S910, the user identification device 100 generates RF signals and scatters the generated RF signals into a body part of the user 110. For example, in the user identification device 100, the transmitter 103 generates the RF signals and scatters the generated RF signals through the transmit antenna 101 into the body part of the user 110. The RF signals scattered into the body part of the user 110 are ultra-wideband signals ranging from 1 GHz to 15 GHz, but the frequency band of the scattered RF signals is not limited thereto. When the user 110 wears the user identification device 100, the user identification device 100 may perform operation S910. Determining of whether the user 110 wears the user identification device 100 may be performed as described above in relation to FIG. 1. Operation S910 is performed after the user identification device 100 stores parameters obtained by training a classification algorithm with the RF signals having passed through the body part of the user 110.

In operation S920, the user identification device 100 receives the RF signals having passed through the body part of the user 110. For example, the user identification device 100 receives the RF signals having passed through the body part of the user 110, through the receive antenna 102 or a receive sensor. When the RF signals scattered from the user identification device 100 are ultra-wideband signals ranging from 1 GHz to 15 GHz, the received RF signals are ultra-wideband signals ranging from 1 GHz to 15 GHz.

In operation S930, the user identification device 100 identifies the user 110 by analyzing the received RF signals based on the trained classification algorithm by using the stored parameters of the trained classification algorithm. The analyzing of the received RF signals based on the trained classification algorithm may indicate classifying of the received RF signals by using the parameters, and determining of whether the classified RF signals correspond to the RF signals having passed through the body part of the user 110. When the classified RF signals correspond to the RF signals having passed through the body part of the user 110, the user identification device 100 obtains a user identification result indicating that the user 110 wearing the user identification device 100 is an owner of the user identification device 100.

FIG. 10 is a flowchart of a classification algorithm training process in a user identification method, according to an embodiment. The process of FIG. 10 may be performed before the user identification method illustrated in FIG. 9 is performed, but is not limited thereto. The process of FIG. 10 may be performed when a user wears the user identification device 100 for the first time. The process of FIG. 10 may be performed on each of a plurality of users. When the process of FIG. 10 is performed on a plurality of users, the user identification device 100 may identify the plurality of users. The process of FIG. 10 may be performed on each of a plurality of gestures of one user. The user may register at least one of the plurality of gestures as a unique signature of the user.

In operation S1010, the user identification device 100 generates RF signals and scatters the generated RF signals into a body part of the user 110 when the body part of the user 110 makes a gesture. In operation S1010, the user identification device 100 may detect whether the user 110 wears the user identification device 100 and then detect whether the user 110 makes a gesture. To this end, the user identification device 100 may use a sensor included in the user identification device 100. The user identification device 100 may request the user 110 to make a predetermined user gesture, before operation S1010. A method of requesting the user 110 to make a user gesture may be performed using the user interface 450 as described above in relation to FIG. 4.

In operation S1020, the user identification device 100 receives the RF signals having passed through the body part of the user 110. When the RF signals scattered in operation S1010 are ultra-wideband signals ranging from 1 GHz to 15 GHz, the received RF signals are ultra-wideband signals ranging from 1 GHz to 15 GHz and distorted through the body part of the user 110.

In operation S1030, the user identification device 100 trains a classification algorithm with the received RF signals and obtains parameters of the trained classification algorithm. The obtained parameters include reference values, variables, or information used to classify the received RF signals into RF signals corresponding to the user 110 or/and the user gesture, based on the trained classification algorithm.

In operation S1040, the user identification device 100 stores the obtained parameters. When the parameters are stored, the user identification device 100 may further store additional information in such a manner that each or at least one of the plurality of gestures is registered as a unique signature of the user 110. The stored additional information may indicate that the user gesture identified based on the stored parameters is registered as a unique signature of the user 110.

FIG. 11 is a flowchart of a user identification method according to another embodiment. Operations S1110, S1120, and S1140 illustrated in FIG. 11 are performed similarly to operations S910 to S930 illustrated in FIG. 9.

In operation S1130, the user identification device 100 converts received RF signals into digital signals. In operation S1140, the user identification device 100 identifies the user 110 by analyzing the digital RF signals based on a trained classification algorithm.

FIG. 12 is a flowchart of a classification algorithm training process in a user identification method, according to another embodiment. Operations S1210, S1220, S1240, and S1250 illustrated in FIG. 12 are performed similarly to operations S1010 to S1040 illustrated in FIG. 10.

In operation S1230, the user identification device 100 converts received RF signals into digital signals. In operation S1240, the user identification device 100 obtains parameters by training a classification algorithm with the digital RF signals.

FIG. 13 is a flowchart of a user identification method according to another embodiment. The method of FIG. 13 further includes an operation of transmitting a user identification result to an external device, compared to the method of FIG. 9. Operations S1310 to S1330 of FIG. 13 are performed similarly to operations S910 to S930 of FIG. 9.

In operation S1340, the user identification device 100 transmits a user identification result to the external device 120. The user identification device 100 may transmit the user identification result to the external device 120 through the communication interface 108 illustrated in FIG. 8. The user identification device 100 may transmit the user identification result to the external device 120 upon a request received through the communication interface 108 from the external device 120. The user identification result may include user authentication information (e.g., user login information or user authentication password information). The user authentication information may be pre-stored in the user identification device 100. The user identification result may replace the user authentication information.

FIG. 14 is a flowchart of a user identification method according to another embodiment. The method of FIG. 14 further includes an operation of transmitting a user identification result and an identified user gesture to an external device, compared to the method of FIG. 9. Operation S1410 and S1420 of FIG. 14 are performed similarly to operations S910 and S920 of FIG. 9.

In operation S1430, the user identification device 100 identifies the user 110 and a user gesture by analyzing received RF signals based on a trained classification algorithm by using stored parameters. The stored parameters may include information capable of classifying received RF signals per user and per user gesture.

In operation S1440, the user identification device 100 transmits the user identification result and the user gesture identification result through the communication interface 108 of FIG. 8 to the external device 120. When a request is received through the communication interface 108 from the external device 120, the user identification device 100 may transmit the user identification result and the user gesture identification result to the external device 120.

FIG. 15 is a flowchart of a user authentication method according to an embodiment. The method of FIG. 15 is performed by a device 1510 having a user identification function according to the disclosure, an external device 1520, and a payment system 1530.

In operation S1501, the device 1510 identifies a user by using RF signals according to the disclosure. After the user is identified, a connection between the device 1510 and the external device 1520 is established (S1502), the external device 1520 performs information input processing based on an event (S1503), and the device 1510 receives a user authentication request based on the event (S1504) and transmits user identification information to the external device 1520 (S1505). The user identification information may include user authentication information stored in the device 1510, and may be used as the user authentication information.

The information input processing performed based on the event in operation S1503 may include, for example, information input for ticketing. For example, to get a train ticket, the above-described information may include departure place information, destination information, boarding time information, and passenger information. The above-described information may be directly input to the external device 1520 by the user wearing the device 1510. For example, the external device 1520 may be a smartphone or a ticket machine installed at a train station. The ticket machine may be a device having a communication function. When the external device 1520 is the smartphone, the above-described information input processing may be performed based on a ticketing application executed by the external device 1520. The establishing of the connection between the device 1510 and the external device 1520 in operation S1502 may be performed when the user authentication request is received in operation S1504 after the information input processing is completed in operation S1503. Owners of the external device 1520 and the device 1510 may be the same or be different.

When the user identification information is received from the device 1510, in operation S1506, the external device 1520 transmits a payment processing request based on the user identification information to the payment system 1530. The payment system 1530 may be an Internet-based payment server.

The payment system 1530 obtains information about the device 1510 based on the received user identification information, and establishes a connection between the device 1510 and the payment system 1530 based on the obtained information about the device 1510 (S1507). To this end, the payment system 1530 may include a database storing mapping information between the user identification information and the information about the device 1510. The information about the device 1510 includes information for the connection to the device 1510 based on a communication network such as the Internet.

When the connection to the device 1510 is established, in operation S1508, the payment system 1530 transmits, to the device 1510, a user authentication request for payment. As such, in operation S1509, the device 1510 transmits the user identification information to the payment system 1530. The payment system 1530 performs payment processing base on the user identification information when the user identification information is received from the device 1510, and transmits payment completion notification information to the external device 1520 (S1510) when the payment processing is completed. As such, the external device 1520 outputs a payment completion notification message to notify the user of the device 1510 of completion of payment. The payment system 1530 may transmit the payment completion notification information to the device 1510 together with the external device 1520. The external device 1520 may output the payment completion notification by using an audio signal or/and an image signal.

Technical features of the disclosure will become apparent from the afore-described embodiments and the attached drawings. It will be understood by one of ordinary skill in the art that various changes in form and details may be made in the disclosure without departing from the scope of the disclosure. Therefore, the afore-described embodiments and the attached drawings should be construed as illustrative and not restrictive. Unless otherwise indicated herein, the singular forms in claims are intended to include the plural forms as well.

The afore-described embodiments may be implemented in the form of a computer-readable recording medium having computer-executable instructions and data recorded thereon. The instructions may be stored in the form of program codes, and may generate a predetermined program module to perform a predetermined operation when executed by a processor. In addition, the instructions may perform predetermined operations of the afore-described embodiments when executed by a processor.

The invention claimed is:

1. A user identification device using radio-frequency (RF) radar, the user identification device comprising:
    a transmitter for transmitting RF signals into a wrist part of a user;
    a receiver for receiving the RF signals transmitted from the transmitter and having passed through the wrist part of the user;
    a memory for storing parameters of a classification algorithm trained with the RF signals having passed through the wrist part of the user based on a plurality of user gestures; and
    a processor for identifying the user and a user gesture by analyzing the received RF signals based on the trained classification algorithm by using the parameters in response to receiving the RF signals having passed through the wrist part, through the receiver, and performing an operation corresponding to the identified user gesture based on an identification result of the user.

2. The user identification device of claim 1, further comprising a user interface,
    wherein the processor requests the user to make each user gesture of the plurality of user gestures, through the user interface, obtains the parameters by training the classification algorithm with the RF signals having passed through the wrist part of the user, based on each of the plurality of user gestures, and stores the obtained parameters in the memory.

3. The user identification device of claim 1, wherein the processor scatters the RF signals into the wrist part of the user through the transmitter, obtains the parameters by training the classification algorithm with the RF signals when the RF signals having passed through the wrist part of the user are received through the receiver, and stores the obtained parameters in the memory.

4. The user identification device of claim 1, further comprising a communication interface for communicating with an external device,
    wherein the processor transmits the identification result of the user and a command corresponding to the identified user gesture through the communication interface to the external device.

5. The user identification device of claim 1, wherein the processor controls the user identification device to continuously identify the user by using the transmitter and the receiver.

6. The user identification device of claim 1,
    wherein the transmitter comprises a transmit antenna, and the receiver comprises a receive antenna, and
    wherein the user identification device further comprises a converter for converting the RF signals received through the receiver, into digital signals.

7. The user identification device of claim 1,
    wherein the user identification device is integrated with a wearable device, and wherein the processor comprises a processor of the wearable device.

8. The user identification device of claim 1, wherein the RF signals comprise ultra-wideband signals.

9. A user identification method performed by a device by using radio-frequency (RF) radar, the user identification method comprising:
  generating, by a transmitter of the device, RF signals and scattering the generated RF signals into a wrist part of a user;
  receiving, by a receiver of the device, the RF signals having passed through the wrist part of the user;
  analyzing, by a processor of the device, the received RF signals by using parameters of a classification algorithm trained with the RF signals having passed through the wrist part of the user based on a plurality of user gestures;
  identifying, by the processor, the user and a user gesture based on an analysis result; and
  performing an operation corresponding to the identified user gesture based on an identification result of the user.

10. The user identification method of claim 9, further comprising:
  requesting the user to make each user gesture of the plurality of user gestures, through a user interface of the device;
  obtaining, by the processor, the parameters by training the classification algorithm with the RF signals having passed through the wrist part of the user, based on each of the plurality of user gestures; and
  storing, by the processor, the obtained parameters in a memory of the device.

11. The user identification method of claim 9, further comprising:
  scattering the RF signals through the transmitter of the device into the wrist part of the user;
  receiving the RF signals having passed through the wrist part of the user, through the receiver of the device;
  obtaining, by the processor, the parameters by training the classification algorithm with the received RF signals; and
  storing, by the processor, the obtained parameters in a memory of the device.

12. The user identification method of claim 9, further comprising transmitting the identification result of the user and a command corresponding to the identified user gesture through a communication interface of the device to an external device.

13. The user identification method of claim 9, wherein the scattering of the RF signals into the wrist part of the user, the receiving of the RF signals having passed through the wrist part of the user, the analyzing of the received RF signals, and the identifying of the user and the user gesture are continuously performed.

14. The user identification method of claim 9, wherein the RF signals comprise ultra-wideband signals.

15. A computer-readable recording medium having recorded thereon computer program code for executing a user identification method, wherein the user identification method comprises:
  generating, by a transmitter of a device, radio-frequency (RF) signals and scattering the generated RF signals into a wrist part of a user;
  receiving, by a receiver of the device, the RF signals having passed through the wrist part of the user;
  analyzing, by a processor of the device, the received RF signals by using parameters of a classification algorithm trained with the RF signals having passed through the wrist part of the user based on a plurality of user gestures;
  identifying, by the processor, the user and a user gesture based on an analysis result; and
  performing an operation corresponding to the identified user gesture based on an identification result of the user.

* * * * *